(12) United States Patent
Slover et al.

(10) Patent No.: US 12,290,287 B2
(45) Date of Patent: May 6, 2025

(54) DISPOSABLE INTERSPINOUS IMPLANT INSERTION INSTRUMENT

(71) Applicant: Spinal Simplicity, LLC, Overland Park, KS (US)

(72) Inventors: Jeff Slover, Lee's Summit, MO (US); Adam Frock, Lenexa, KS (US); Todd Moseley, Olathe, KS (US); Jeffrey David Lee, Prairie Village, KS (US); Christian Aragonez, Kansas City, MO (US); Adam Rogers, Overland Park, KS (US); Melissa Frock, Lenexa, KS (US)

(73) Assignee: Spinal Simplicity, LLC, Overland Park, KS (US)

( * ) Notice: Subject to any disclaimer, the term of this patent is extended or adjusted under 35 U.S.C. 154(b) by 52 days.

(21) Appl. No.: 18/311,048

(22) Filed: May 2, 2023

(65) Prior Publication Data

US 2023/0320764 A1 Oct. 12, 2023

Related U.S. Application Data

(63) Continuation of application No. 17/716,833, filed on Apr. 8, 2022, now Pat. No. 11,672,572.

(51) Int. Cl.
*A61B 17/70* (2006.01)
*A61F 2/46* (2006.01)

(52) U.S. Cl.
CPC ...... *A61B 17/7067* (2013.01); *A61B 17/7074* (2013.01); *A61F 2/4611* (2013.01)

(58) Field of Classification Search
CPC ............. A61F 2/4611; A61B 17/77067; A61B 17/7074
See application file for complete search history.

(56) References Cited

U.S. PATENT DOCUMENTS

| 5,885,229 A * | 3/1999 | Yamato ................ A61B 5/1038 600/592 |
| 6,004,326 A * | 12/1999 | Castro ................ A61B 17/1604 606/99 |
| 2012/0095560 A1* | 4/2012 | Donner ................ A61F 2/4455 623/17.11 |
| 2017/0296238 A1* | 10/2017 | Snell ................... A61B 17/7082 |
| 2018/0161171 A1* | 6/2018 | Frasier .................... A61F 2/447 |
| 2019/0021868 A1* | 1/2019 | Ludwig ................ A61F 2/4611 |
| 2023/0372122 A1* | 11/2023 | Martin ...................... A61F 2/44 |

* cited by examiner

*Primary Examiner* — Matthew J Lawson
(74) *Attorney, Agent, or Firm* — Erise IP, P.A.

(57) ABSTRACT

A disposable insertion instrument for inserting an implant includes a handle assembly, a drive assembly, and a plunger assembly. The drive assembly comprises an inner shaft and a spring received within an outer sleeve. A locking pin and drive lobes on the inner shaft cooperate to reversibly lock the drive assembly in a retracted position. A medical implant may be attached to the instrument via an adapter located at a distal end of the drive assembly. Following use for insertion of the medical implant into a patient, the disposable insertion instrument may be discarded.

20 Claims, 14 Drawing Sheets

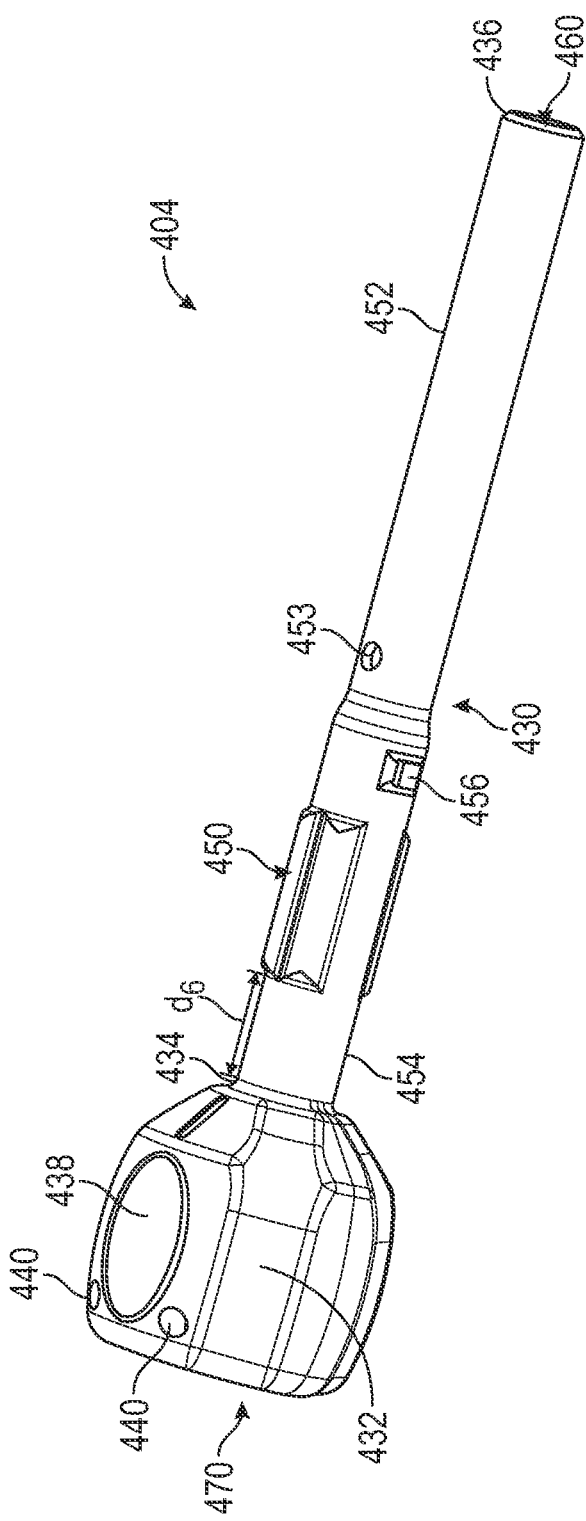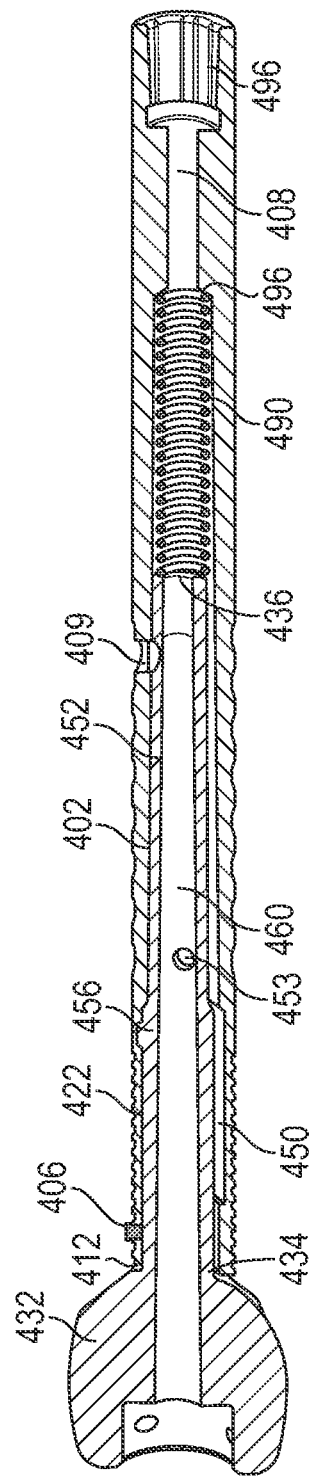
FIG. 7A
FIG. 7B

DISPOSABLE INTERSPINOUS IMPLANT INSERTION INSTRUMENT

CROSS-REFERENCE TO RELATED APPLICATIONS

This patent application is a continuation application claiming priority benefit, with regard to all common subject matter, of U.S. patent application Ser. No. 17/716,833, filed Apr. 8, 2022, and entitled "DISPOSABLE INTERSPINOUS IMPLANT INSERTION INSTRUMENT." The above-referenced application is hereby incorporated by reference in its entirety into the present application.

BACKGROUND

1. Field

The subject technology is directed to instruments for inserting implants into a patient. More particularly, embodiments of the invention relate to a disposable insertion instrument for inserting an interspinous implant.

2. Related Art

The spine consists of a column of twenty-four vertebrae that extend from the skull to the hips. Discs of soft tissue are disposed between adjacent vertebrae. The vertebrae provide support for the head and body, while the discs act as cushions. In addition, the spine encloses and protects the spinal cord, defining a bony channel around the spinal cord, called the spinal canal. There is normally a space between the spinal cord and the borders of the spinal canal so that the spinal cord and the nerves associated therewith are not pinched.

Over time, the ligaments and bone that surround the spinal canal can thicken and harden, resulting in a narrowing of the spinal canal and compression of the spinal cord or nerve roots. This condition is called spinal stenosis, which results in pain and numbness in the back and legs, weakness and/or a loss of balance. These symptoms often increase after walking or standing for a period of time.

There are a number of non-surgical treatments for spinal stenosis. These include non-steroidal anti-inflammatory drugs to reduce the swelling and pain, and corticosteroid injections to reduce swelling and treat acute pain. While some patients may experience relief from symptoms of spinal stenosis with such treatments, many do not, and thus turn to surgical treatment. Some surgical procedures for treating spinal stenosis are decompressive laminectomy and interspinous process decompression (IPD). A well-known implant used for performing IPD surgery is the X-STOP® device, which is described in U.S. Pat. No. 6,419,676, the disclosure of which is herein incorporated by reference in its entirety. Another interspinous process implant placed in a minimally invasive surgical procedure is disclosed in U.S. Pat. No. 9,545,267, which is also incorporated herein by reference in its entirety.

Examples of particularly useful interspinous process implant and fusion devices are disclosed in commonly assigned U.S. Pat. Nos. 9,861,399, 8,945,184; 9,314,276, 9,907,581, 9,757,164, U.S. Patent Application Publication No. 2022/0054279, U.S. Patent Application Publication No. 2022/0054280, and U.S. application Ser. No. 17/677,677, the disclosures of which are all incorporated herein by reference in their entirety.

One aspect of effective insertion of these implants is to provide a low profile instrument for deploying the implant. Often, the insertion instrument has several moving parts. Because of the cost of the insertion instruments, the instruments are generally reused many times. For such insertion instruments to be reused, the insertion instruments must be properly and fully cleaned without damage or loss of the components. Exemplary re-usable insertion instruments are disclosed in commonly assigned U.S. Pat. No. 10,420,591 and U.S. Patent Application Publication No. 2020/0015864.

SUMMARY

Embodiments of the invention solve the above-mentioned problems by providing a disposable insertion instrument for the insertion of a medical implant into the spinous region of a patient. With the ever-increasing cost of raw materials due to supply chain issues and labor shortages, traditional metal insertion instruments face raising costs and difficulties in producing mass quantities of re-usable insertion instruments. Disposable insertion instruments, due to being disposed of after a single use, may be constructed from plastics or other polymers that are not required to withstand repeated uses, eliminating the need to use more expensive durable materials. Further, instruments constructed from plastics or other polymers may be constructed using relatively simple molding procedures, rather than assembly line or other intensive manufacturing processes. Accordingly, the present invention provides a low-cost, but effective alternative to reusable implant insertion instruments.

In some aspects, the techniques described herein relate to a disposable insertion instrument for inserting an implant, the insertion instrument including: a handle assembly including a handle knob and an elongated main body extending distally therefrom, the elongated main body including a proximal end, a distal end, and a lumen extending therebetween, the distal end configured to engage the implant; a plunger assembly slidably received within the lumen of the elongated main body, the plunger assembly including a plunger knob and a plunger shaft, wherein a distal end of the plunger shaft is configured to engage the implant; and a spring-loaded drive assembly including an outer sleeve, an inner shaft, and a locking pin, wherein the outer sleeve has a recessed region, and wherein the inner shaft includes an inner shaft knob, an inner shaft main body, and at least one drive lobe on the inner shaft main body, the at least one drive lobe being received within the recessed region, wherein the spring-loaded drive assembly includes a first extended position and second retracted position, wherein the locking pin is located proximally of the at least one drive lobe in the retracted position, and wherein the locking pin is located adjacent to the at least one drive lobe in the extended position.

In some aspects, the techniques described herein relate to a disposable insertion instrument, wherein the at least one drive lobe includes a raised region on an exterior circumference of the inner shaft main body.

In some aspects, the techniques described herein relate to a disposable insertion instrument, wherein the at least one drive lobe includes at least two drive lobes, the locking pin is fixedly mounted to the outer sleeve, and the locking pin is located between the at least two drive lobes in the extended position.

In some aspects, the techniques described herein relate to a disposable insertion instrument, wherein the outer sleeve is configured to be rotated and moved proximally with respect to the inner shaft to move the spring-loaded drive assembly from the extended position to the retracted position.

In some aspects, the techniques described herein relate to a disposable insertion instrument, wherein the handle knob, the inner shaft, and the outer sleeve include polymeric materials.

In some aspects, the techniques described herein relate to a disposable insertion instrument, wherein the inner shaft main body has an inner lumen therethrough, the elongated main body being received within the inner lumen of the inner shaft main body.

In some aspects, the techniques described herein relate to a medical implant insertion system including: a disposable insertion instrument including: a handle assembly including an elongated main body, the elongated main body including a proximal end, a distal end, and a main body lumen extending therebetween, the distal end configured to engage the implant; a plunger assembly longitudinally movable within the main body lumen of the elongated main body, the plunger assembly including a plunger shaft, wherein a distal end of the plunger shaft is configured to engage the implant; and a drive assembly including an outer sleeve having a drive lumen with a recessed region, and an inner shaft main body received within the drive lumen, the inner shaft main body having an inner lumen therethrough and at least one drive lobe on an exterior circumference thereof, the elongated main body being received within the inner lumen, and the at least one drive lobe being received within the recessed region of the outer sleeve.

In some aspects, the techniques described herein relate to a system, further including: an implant adapter including a proximal end and a distal end, the proximal end of the implant adapter including at least one flexible leg reversibly attached to a distal end of the outer sleeve of the drive assembly, and the distal end of the implant adapter configured to engage a proximal end of the implant.

In some aspects, the techniques described herein relate to a system, wherein the outer sleeve and the inner shaft main body are composed of polymeric materials.

In some aspects, the techniques described herein relate to a system, wherein the drive assembly further includes a spring located at the distal end of the inner shaft main body, the drive assembly having a first extended position where the spring is relaxed, and a second retracted position where the spring is compressed.

In some aspects, the techniques described herein relate to a system, wherein the drive assembly further includes a locking pin, wherein the locking pin is located proximally of the at least one drive lobe in the retracted position, and wherein the locking pin is located adjacent to the at least one drive lobe in the extended position.

In some aspects, the techniques described herein relate to a system, wherein the distal end of the plunger shaft includes external threading configured to engage an implant plunger, and wherein the distal end of the main body includes a hexagonal extension configured to engage a proximal bore of the implant.

In some aspects, the techniques described herein relate to a method of inserting a medical implant using a disposable insertion instrument, the method including: providing the disposable insertion instrument including: a handle assembly including an elongated main body, the elongated main body including a proximal end, a distal end configured to engage the implant, and a main body lumen extending therebetween; a spring-loaded drive assembly including an outer sleeve having a distal end configured to engage an implant adapter and a drive lumen with a recessed region, and an inner shaft main body having an inner lumen therethrough and at least one drive lobe on an exterior circumference thereof; and a plunger assembly including a plunger shaft having a distal end configured to engage the implant; and receiving the inner shaft main body within the drive lumen of the outer sleeve of the drive assembly, wherein the at least one drive lobe is received within the recessed region; receiving the elongated main body of the handle assembly within the inner lumen of the inner shaft main body of the drive assembly; and receiving the plunger shaft within the main body lumen of the elongated main body such that the plunger shaft is longitudinally movable therein.

In some aspects, the techniques described herein relate to a method, further including: attaching the implant adapter to the distal end of the outer sleeve of the drive assembly; retracting the outer sleeve of the drive assembly against a force of a spring such that the distal end of the elongated main body extends distally from the distal end of the implant adapter; and rotating the outer sleeve with respect to the inner shaft of the drive assembly, such that a locking pin is seated proximally of the at least one drive lobe to maintain the outer sleeve in a retracted position.

In some aspects, the techniques described herein relate to a method, further including: while the outer sleeve is locked in the retracted position, attaching the implant to the elongated main body, the implant including: an implant main body, two expandable distal wings connected by linkages to an implant plunger, and a proximal nut.

In some aspects, the techniques described herein relate to a method, wherein attaching the implant includes: inserting the distal end of the elongated main body into a proximal bore of the implant while the plunger shaft is in the retracted position.

In some aspects, the techniques described herein relate to a method, wherein the distal end of the elongated main body includes flexible arms, and wherein attaching the implant further includes: advancing the plunger shaft distally to engage the implant and lock the flexible arms of the elongated main body to the implant.

In some aspects, the techniques described herein relate to a method, wherein attaching the implant further includes: inserting the distal end of the plunger shaft into an implant plunger bore of the implant plunger; and rotating the plunger shaft to engage internal threads of the implant plunger bore with external threads of the plunger shaft.

In some aspects, the techniques described herein relate to a method, wherein attaching the implant further includes: connecting the distal end of the implant adapter to the implant by receiving the proximal nut of the implant in a plurality of adapter grooves of the implant adapter.

In some aspects, the techniques described herein relate to a method, further including: inserting the distal end of the insertion instrument to a target region of a patient, upon reaching the target region, rotating the handle assembly to thread the implant into the bone; longitudinally advancing the plunger shaft to deploy the distal wings of the implant; and rotating the drive assembly with respect to the handle assembly to rotate the proximal nut on the implant.

This summary is provided to introduce a selection of concepts in a simplified form that are further described below in the detailed description. This summary is not intended to identify key features or essential features of the claimed subject matter, nor is it intended to be used to limit the scope of the claimed subject matter. Other aspects and advantages of the present invention will be apparent from the following detailed description of the embodiments and the accompanying drawing figures.

BRIEF DESCRIPTION OF THE DRAWING FIGURES

Embodiments of the invention are described in detail below with reference to the attached drawing figures, wherein:

FIG. 7A is a perspective view of an inner shaft of the drive assembly in accordance with some embodiments of the invention;

FIG. 7B depicts a cross-sectional view of an embodiment of the drive assembly in an assembled configuration;

Figure 12:
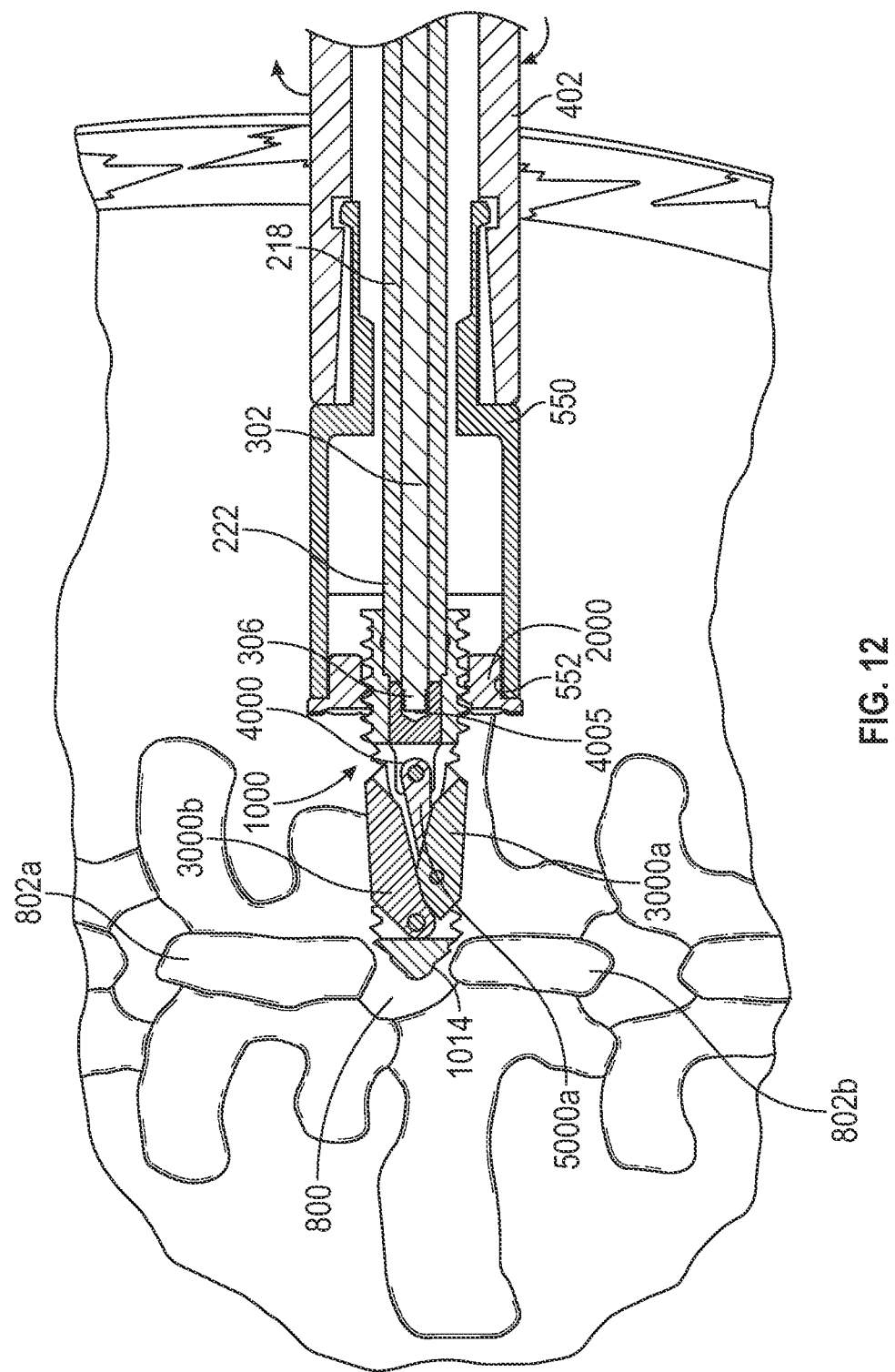
Figure 13:
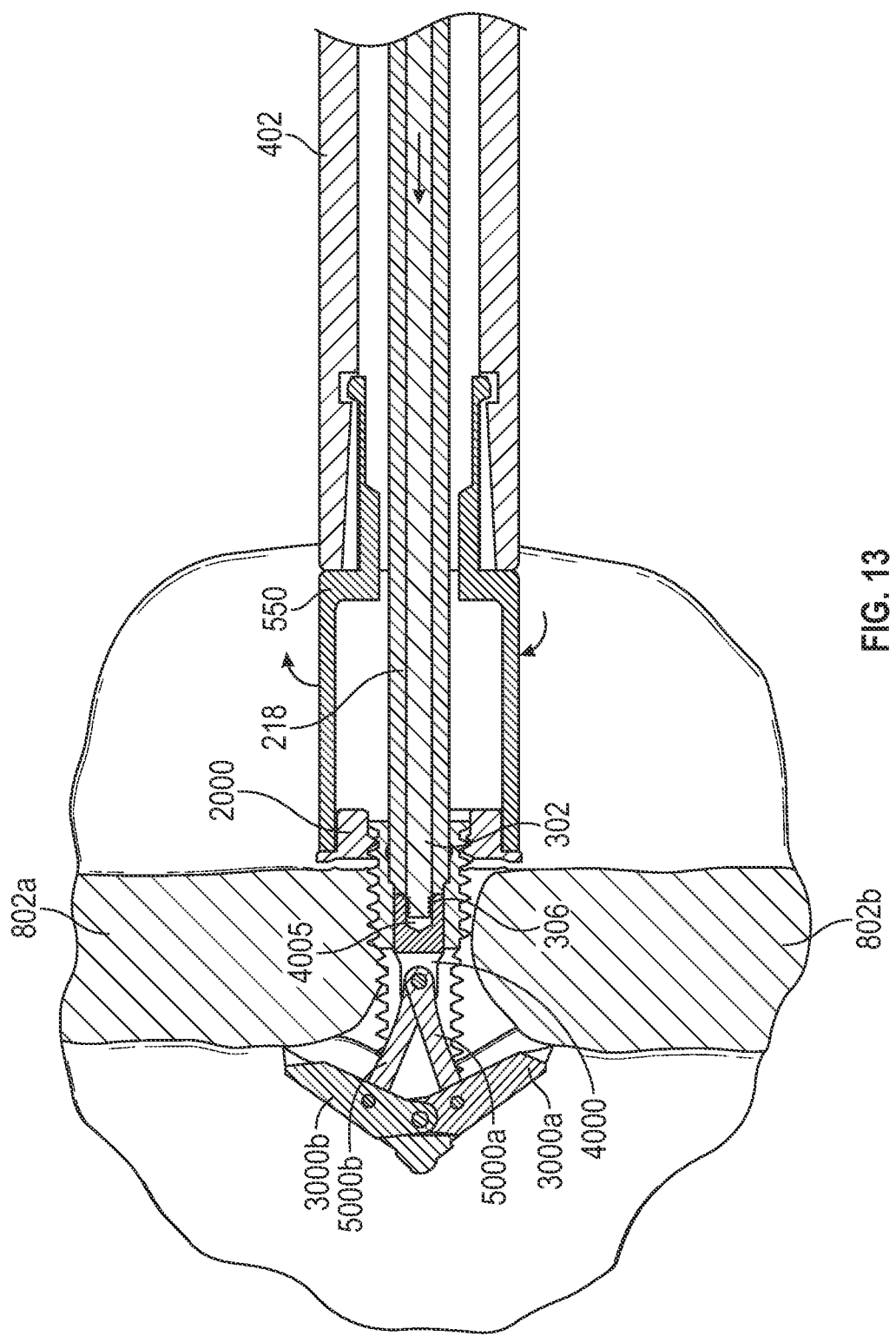

FIG. 12 is a cross-sectional view of a medical implant in a closed configuration being inserted into an interspinous region via the disposable insertion instrument in accordance with some embodiments of the invention; and FIG. 13 is a cross-sectional view of a medical implant in a deployed configuration being inserted into an interspinous region via the disposable insertion instrument in accordance with some embodiments of the invention.

The drawing figures do not limit the invention to the specific embodiments disclosed and described herein. The drawings are not necessarily to scale, emphasis instead being placed upon clearly illustrating the principles of the invention.

DETAILED DESCRIPTION

The following detailed description of embodiments of the invention references the accompanying drawings that illustrate specific embodiments in which the invention can be practiced. The embodiments are intended to describe aspects of the invention in sufficient detail to enable those skilled in the art to practice the invention. Other embodiments can be utilized, and changes can be made without departing from the scope of the present invention. The following detailed description is, therefore, not to be taken in a limiting sense. The scope of the invention is defined only by the appended claims, along with the full scope of equivalents to which such claims are entitled.

In this description, references to "one embodiment," "an embodiment," or "embodiments" mean that the feature or features being referred to are included in at least one embodiment of the technology. Separate references to "one embodiment," "an embodiment," or "embodiments" in this description do not necessarily refer to the same embodiment and are also not mutually exclusive unless so stated and/or except as will be readily apparent to those skilled in the art from the description. For example, a feature, structure, act, etc. described in one embodiment may also be included in other embodiments but is not necessarily included. Thus, the present technology can include a variety of combinations and/or integrations of the embodiments described herein.

Broadly, embodiments of the present invention relate to a disposable insertion instrument for the insertion of a medical implant. The disposable insertion instrument may comprise various sub-assemblies that facilitate the insertion and deployment of a medical implant in the spinal region of a patient. A disposable spring-loaded drive assembly may receive an implant on the distal end. Further, some parts of the disposable insertion instrument, such as the handle and drive assembly, may be constructed from polymeric materials or plastics, providing for a single-use, disposable instrument. Accordingly, the design of the disposable insertion instrument may be simpler and less expensive than re-usable instruments that require sterilization.

Figure 1:
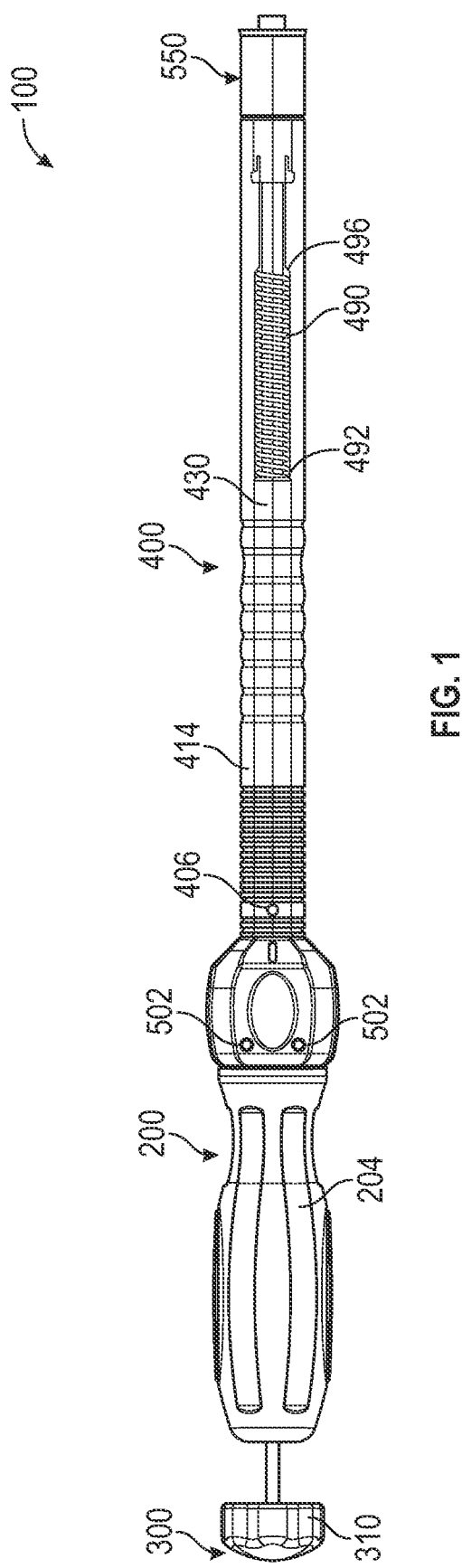
FIG. 1 is a perspective view of a disposable insertion instrument shown with an attached adapter with the drive assembly and the plunger assembly both in a retracted position in accordance with some embodiments of the invention.
Figure 2:
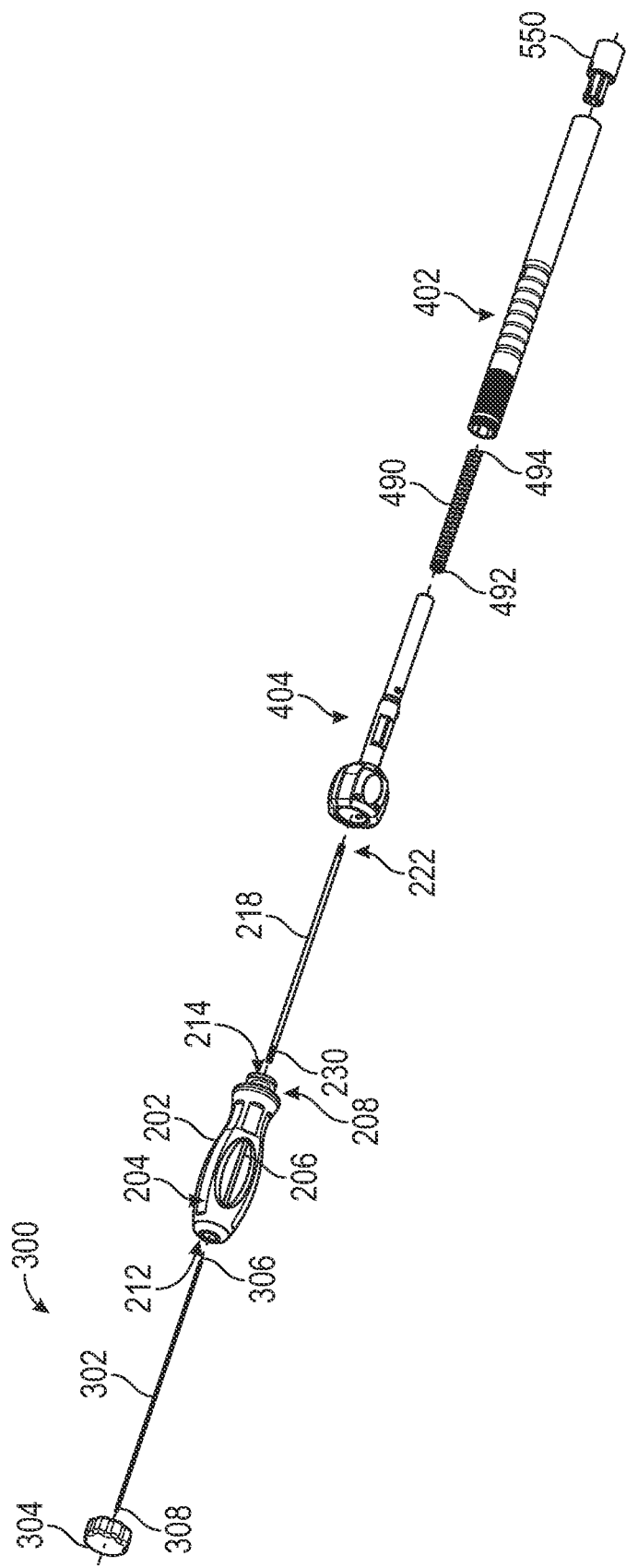
FIG. 2 is an exploded view showing the various sub-assemblies of the insertion instrument of FIG. 1.
Figure 4:
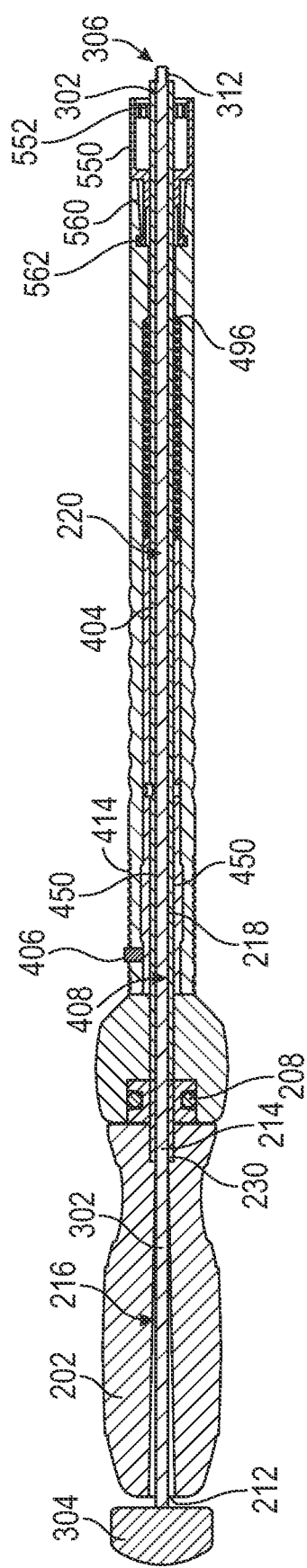
FIG. 4 is a longitudinal cross-sectional view of the disposable insertion instrument of FIG. 1.

FIG. 1 is a perspective view of a disposable insertion instrument 100 for inserting an implant. Exemplary implants that can be inserted with the insertion instrument of the present invention are disclosed above. In some embodiments, disposable insertion instrument 100 may comprise various sub-assemblies that may be used in conjunction to operate disposable insertion instrument 100. In some embodiments, disposable insertion instrument 100 may generally comprise: a handle assembly 200, a plunger assembly 300, a drive assembly 400, and an implant adapter 550. FIG. 2 shows an exploded view of the various sub-assemblies. As best depicted in FIG. 4, handle assembly 200 provides a lumen for receiving plunger assembly 300 therethrough. When drive assembly 400 is in a retracted position, as seen in FIGS. 1 and 4, a distal end of plunger assembly 300 extends out of distal end of the implant adapter 550 for receiving an implant thereon.

Handle Assembly

Figure 3A:
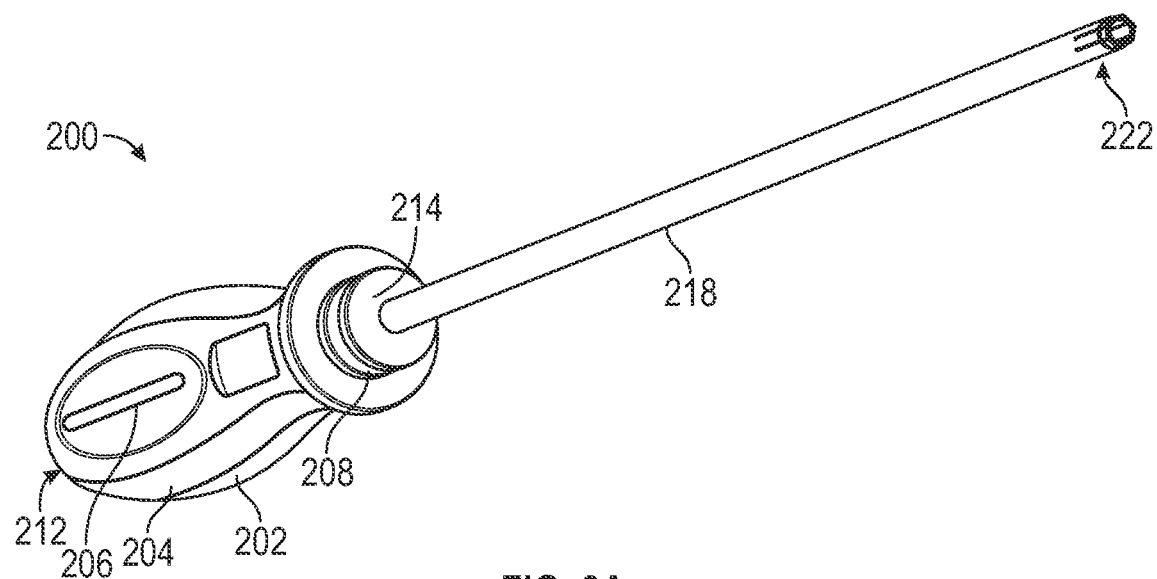
FIG. 3A is a perspective view of the handle assembly of disposable insertion instrument of FIG. 1.
Figure 3B:
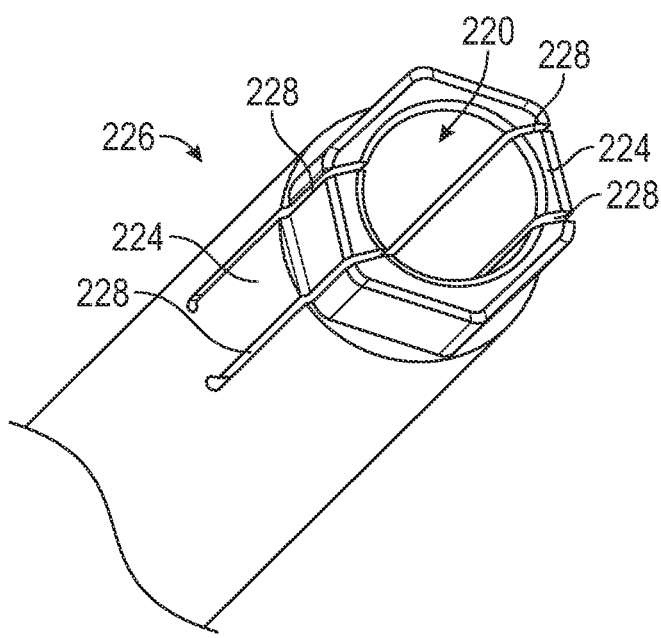
FIG. 3B is a perspective view of the distal end of the handle assembly of FIG. 3A.
Figure 8:
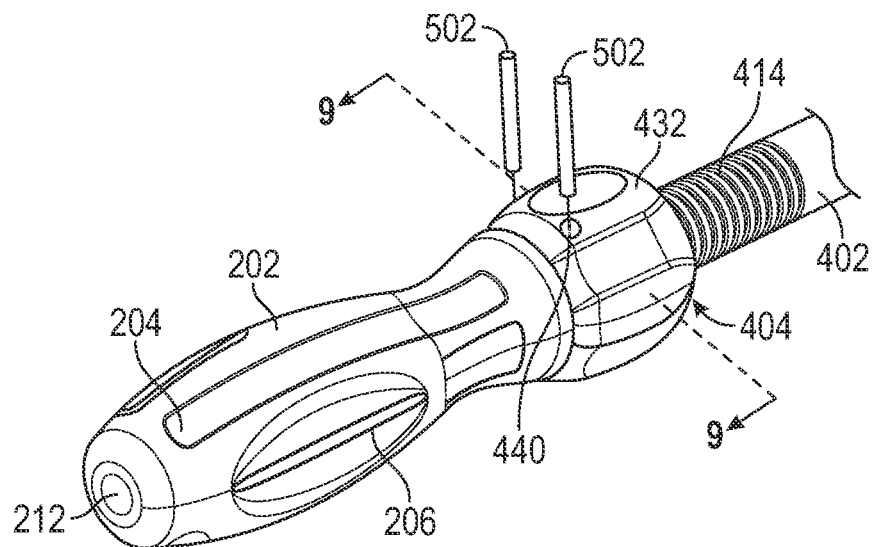
FIG. 8 is a perspective view of a handle, pins, and drive assembly of a disposable insertion instrument in accordance with some embodiments of the invention.

As seen in FIGS. 3A-B and 8, in some embodiments, the handle assembly 200 may generally provide a first graspable or manipulative engagement area of disposable insertion instrument 100. With respect to FIG. 3A, in some embodiments, handle assembly 200 may generally comprise a handle 202, which may be shaped or configured to accept the hand of an operator, and an elongated main body 218. For example, in some embodiments, handle 202 may generally comprise an elongated, cylindrical design, similar to a screwdriver or other similar hand operable tool. In some embodiments, handle 202 may comprise one or more gripping aids 204, which may aid an operator or user in handling disposable insertion instrument 100. For example, gripping aids 204 may be grooves or recesses defined in handle 202, providing a tactile aid. In further embodiments, gripping aids 204 may be selectively placed textured areas, providing a gripping effect between handle 202 and the operator or user, including for example a rubber textured surface. In some embodiments, handle 202 may further comprise at least one wing indicator 206. In some embodiments, handle 202 includes two wing indicators 206, which provide a reference to the location of the wings of a medical implant to be attached to the distal end of the main body 218. In some embodiments, handle 202 may further comprise a circumferential groove 208 located near a distal end. As described in greater detail below, circumferential groove 208 may be configured accept one or more retaining pins 502 for connecting handle assembly 200 to drive assembly 400.

As seen in FIGS. 2 and 3A, handle 202 comprises a proximal opening 212 and a distal opening 214. With respect to FIG. 4, in some embodiments, handle 202 may be hollow or may otherwise comprise a central handle channel 216 extending therethrough. In some embodiments, handle channel 216 may connect proximal opening 212 to distal opening 214. Main body 218 comprises a proximal end 230, a distal end 222, and a main body lumen 220 extending therebetween. As seen in FIGS. 3A-B, main body 218 comprises a cylindrical shaft having a main body lumen 220 with a substantially circular cross-section. As described in greater detail below, central handle channel 216 and main body lumen 220 of main body 218 cooperate to provide a continuous lumen for receiving plunger shaft 302 of plunger assembly 300.

As seen in FIG. 4, proximal end 230 of main body 218 is received within distal opening 214 of handle 202 and fixedly mounted thereto. Proximal end 230 of main body 218 may connect and/or attach to handle 202 in various ways. For example, in some embodiments proximal end 230 of elongated main body 218 may comprise a threaded feature cooperate with a threaded feature of distal opening 214. In further embodiments, elongated main body 218 may comprise a smooth, or otherwise non-threaded feature and may be inserted into distal opening 214 and retained in position through an interference fit, or other mechanical means. In even further embodiments, elongated main body 218 may be molded or otherwise formed together with handle 202, wherein proximal end 230 is merely the intersection of elongated main body 218 and handle 202. In some embodiments, elongated main body 218 is formed from a metal material or other high-strength material to provide structural rigidity. In some embodiments, handle 202 is formed from a polymeric material or disposable to provide a comfort grip and lower cost and ease in manufacturing.

As seen in FIG. 3B, in some embodiments, elongated main body 218 may further comprise a distal end 222 configured to selectively couple to a medical implant, such as implant 1000. Distal end 222 may include tip 226 having flexible arms 224 that may allow for the expansion and/or compression of tip 226. In some embodiments, flexible arms 224 are formed by slits 228 formed in distal end 222. For example, distal end 222 may include four slits 228 forming two flexible arms 224. In some embodiments, tip 226 may also comprise a generally hexagonal shape of a smaller diameter than the remainder of shaft of main body 218. The generally hexagonal shape of tip 226 may aid in coupling handle assembly 200 to implant 1000 by cooperating with a complementary hexagonal feature or design present in proximal end of implant 1000. In some embodiments, tip 226 may comprise different shapes or designs, and is not limited to a hexagonal shape. For example, in some embodiments tip 226 may comprise a triangular, rectangular, pentagonal, or other polygonal or geometric design. It will be further appreciated that the design of tip 226 may be based at least in part on the corresponding feature of implant 1000, as described below.

Plunger Assembly

Figure 5:
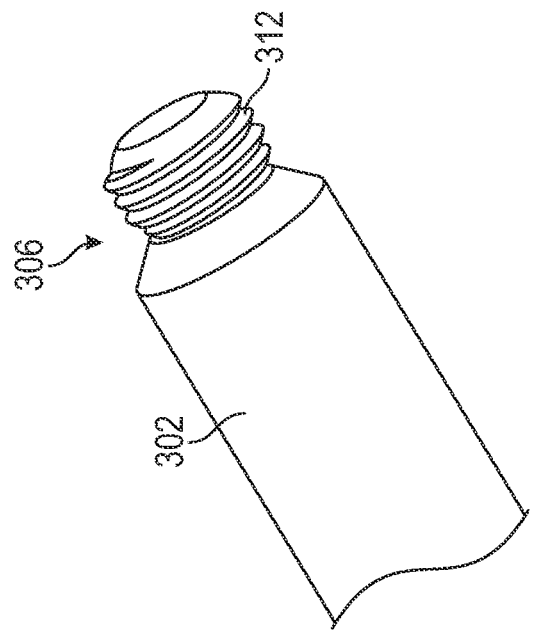
FIG. 5 is an enlarged view of distal end of plunger shaft of plunger assembly.

In some embodiments, disposable insertion instrument 100 may also comprise a plunger assembly 300. As seen in FIGS. 2, 4, and 5, in some embodiments, plunger assembly 300 may generally comprise a plunger shaft 302 and a plunger knob 304. In some embodiments, the plunger shaft 302 may be inserted into proximal opening 212 of handle 202 and may extend through handle channel 216 and through main body lumen 220 and out the distal end. Accordingly, plunger shaft 302 may comprise a smaller outer diameter than the inner diameter of handle channel 216 and main body lumen 220. In some embodiments, plunger shaft 302 may be inserted into handle 202 until plunger knob 304 abuts proximal opening 212. For example, plunger knob 304 may have a larger dimension than proximal opening 212.

In some embodiments, plunger shaft 302 may generally be defined by a distal end 306 and a proximal end 308. In some embodiments, proximal end 308 of plunger shaft 302 may be received within an opening of plunger knob 304 and fixedly mounted thereto. Proximal end 308 of plunger shaft 302 may connect and/or attach to plunger knob 304 in various ways. In some embodiments, proximal end 308 and plunger knob 304 may comprise compatible locking features. For example, in some embodiments, proximal end 308 and plunger knob 304 may comprise compatible threading features. In some embodiments, proximal end 308 and plunger knob 304 may comprise a locking tab feature, wherein proximal end 308 may be inserted into plunger knob 304 and locked in place. In further embodiments, proximal end 308 may be molded or otherwise formed into plunger knob 304, thereby making plunger shaft 302 and plunger knob 304 as a singular unitary piece. In some embodiments, plunger shaft 302 and/or plunger knob 304 are formed from a metal material or other high-strength material to provide structural rigidity.

In some embodiments, plunger knob 304 may be designed as a contact point between a user or operator and the plunger assembly 300. For example, in some embodiments, plunger knob 304 may comprise a generally circular design, providing an engagement point for a user or operator. In some embodiments, plunger knob 304 may further comprise a domed feature. However, it will be appreciated that in further embodiments, plunger knob 304 may comprise other shapes or dimensions, and is not limited to a circular design. For example, in some embodiments, plunger knob 304 may comprise a triangular, rectangular, pentagonal, or other polygonal design. In some embodiments, plunger knob 304 may further comprise one or more gripping aids 310 as seen in FIG. 1, which may aid the user or operator in handling plunger knob 304. For example, in some embodiments, the plunger knob 304 may comprise recessed grooves around a perimeter of plunger knob 304, providing a gripping effect between a user and plunger knob 304. In some embodiments, plunger knob 304 may comprise a shape that acts as a gripping aid. For example, in some embodiments, plunger knob 304 may be designed as a geometric shape having three or more defined sides (e.g., triangle, rectangle, pentagon, hexagon, etc.), wherein the sides of the plunger knob 304 may act as gripping aids 310.

As seen in FIG. 5, in some embodiments, distal end 306 of plunger shaft 302 may comprise an engagement feature 312, which may be configured for engaging the implant 1000. As seen in FIG. 5, In some embodiments, engagement feature 312 may comprise external threading, allowing distal end 306 to screw into implant 1000. Distal end 306 may have a smaller diameter than the remainder of the plunger shaft 302 for being received within hollow bore 1024 on the proximal end of implant 1000 and engaging with central bore 4005 of implant plunger 4000.

In some embodiments, plunger knob 304 may be used to manipulate the positioning of plunger shaft 302 in multiple ways. As seen in FIG. 4, distal end 306 of plunger shaft 302 may extend from distal end of tip 226 of elongated main body 218 when in the longitudinal extended position. This fully extended position is shown in FIG. 4 for illustration purposes without implant 1000 thereon, however it is noted that the plunger shaft 302 would generally be in a longitudinal retracted position until after the implant is anchored onto the distal end of the main body 218 and adapter 550. The plunger assembly 300 may be partially advanced to allow for attachment to the implant 1000. In some embodiments, the rotation of plunger knob 304 and plunger shaft 302 may be used to screw engagement feature 312 into implant plunger 4000 thereby anchoring plunger shaft 302 to implant 1000. Once the plunger shaft 302 is attached to implant plunger 4000, a user may apply a longitudinal force to move plunger shaft 302 axially through handle channel 216 and main body lumen 220. As described in greater detail below, such axial movement may cause the opening or closing of one or more wings 3000*a*, 3000*b* of implant 1000.

Drive Assembly

In some embodiments, disposable insertion instrument 100 may further comprise a spring-loaded drive assembly 400 (FIG. 7B), which may be retracted to expose distal end 306 of plunger assembly 300 and extended to provide a distal force to the implant 1000 during insertion. In some embodiments, drive assembly 400 may further comprise multiple sub-assemblies or parts, including for example, outer sleeve 402 (FIG. 6A-C), inner shaft 404 (FIG. 7A), locking pin 406, and spring 490.

Figure 6A:
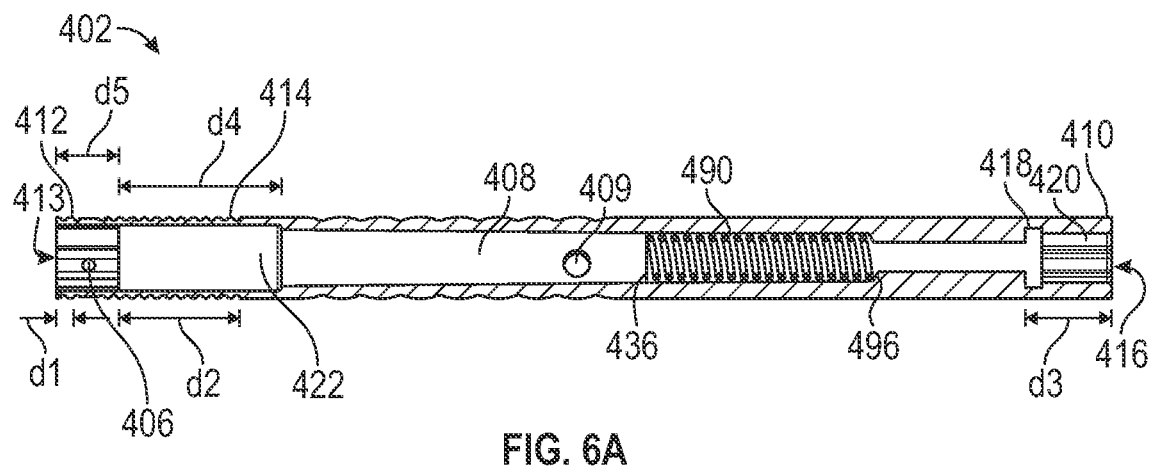
FIG. 6A is a cross-sectional view of an outer sleeve of a drive assembly in accordance with some embodiments of the invention.

As seen in FIG. 6A, outer sleeve 402 may comprise a proximal end 412, a distal end 410, and an axial passage 408 therebetween. Distal end 410 may further be configured for receiving implant adapter 550. In some embodiments, at least a portion of the exterior of outer sleeve 402 may comprise one or more gripping aids 414 (see FIG. 1), which may aid a user or operator in gripping and/or handing disposable insertion instrument 100. For example, gripping aids 414 may be formed directly into outer sleeve 402 as recessed grooves or embossments. In further embodiments, gripping aids 414 may be later applied features, such as rubber grips. As seen in FIG. 6A, gripping aids 414 may be located near proximal end 412. A first set of gripping aids 414 may be provided adjacent to the proximal end 412 extending along a distance d1, and a second set of gripping aids 414 may be provided extending along a distance d2 from the proximal end 412. A locking pin 406 may be fixedly mounted within a hole in outer sleeve 402. Locking pin 406 may be located between the two sets of gripping aids 414, as seen in FIG. 6A. In some embodiments, locking pin 406 may be made of a metal material. Locking pin 406 may be mounted within outer sleeve 402 such as by an interference fit, adhesive, welding, or other mechanical means. In some embodiments, outer sleeve 402 comprises a thermoplastic material. In some embodiments, outer sleeve 402 may also comprise a central hole 409 located proximally of spring 490 for use in an injection molding manufacturing process.

Distal end 410 may comprise an adapter channel 416, which may be configured for accepting implant adapter 550, for receiving implant 1000 as described in greater detail below. In some embodiments, adapter channel 416 may extend a pre-determined distance d3 from the distal end 410 of outer sleeve 402 to groove 418. The distance d3 may correspond to a compatible implant adapter 550. For example, in some embodiments, one disposable insertion instrument 100 may be designed for use with multiple medical implants 1000 of varying sizes. Additionally, multiple medical adapters 550 for receiving implant 1000 of varying dimensions may be used with disposable insertion instrument 100. In some embodiments, two or three different implant adapters 550 may be configured to receive at least 5 different implant sizes of implant 1000.

Figure 6B:
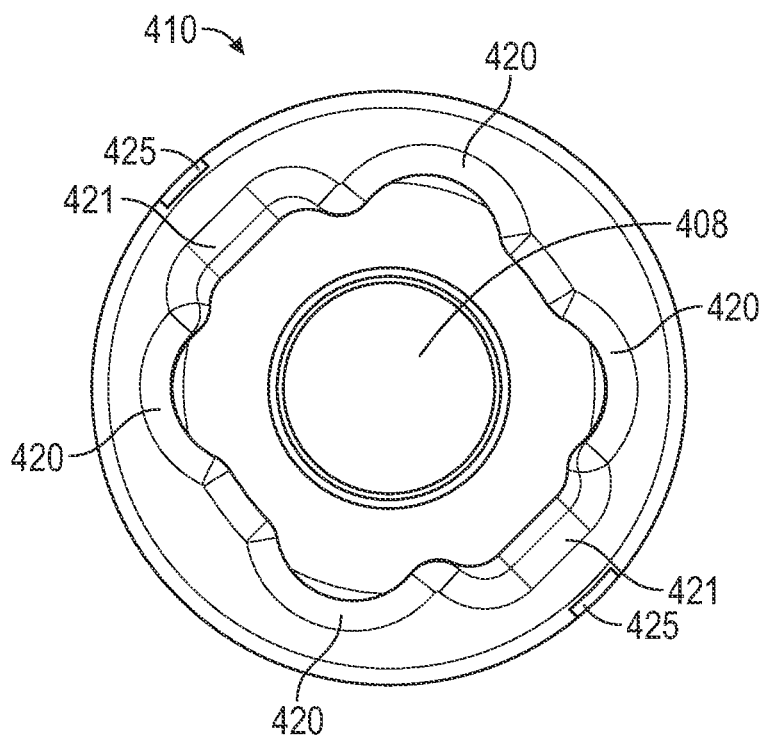
FIG. 6B is an end view of the distal end of an outer sleeve of a drive assembly in accordance with some embodiments of the invention.

In some embodiments, adapter channel 416 may comprise one or more or adapter grooves 420 configured for accepting implant adapter 550. For example, in some embodiments, as seen in FIGS. 6A and 6B, adapter channel 416 may comprise four adapter grooves 420, comprising a generally four leaf clover-like orientation. Adapter channel 416 may also have two additional sides 421 for receiving legs 560 of implant adapter 550. Outer surface of sleeve 402 includes an alignment groove 425, as seen in FIG. 6B. As described in greater detail below, the implant adapter 550 may engage the adapter grooves 420 thereby securing the implant adapter 550 in place. It will be appreciated that adapter channel 416 may optionally or additionally comprise any number of adapter recesses and may further orient adapter grooves 420 in any configuration. For example, in some embodiments, adapter channel 416 may comprise five adapter grooves 420 oriented in a pentagonal configuration.

Figure 6C:
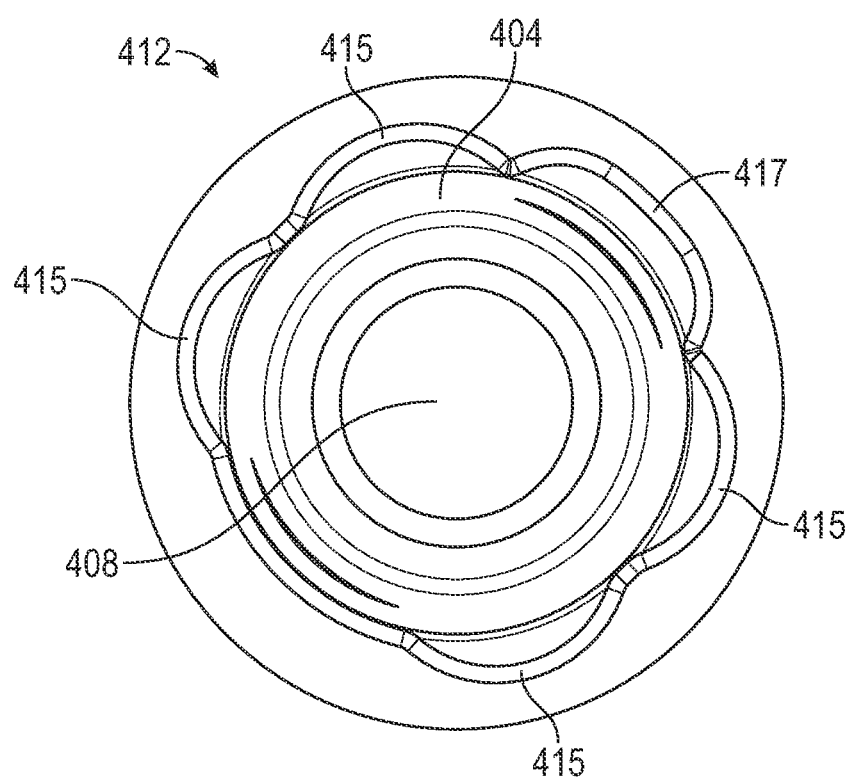
FIG. 6C is an end view of the proximal end of an outer sleeve of a drive assembly in accordance with some embodiments of the invention.

In some embodiments, proximal end 412 of outer sleeve 402 may further comprise a recessed region 422. In some embodiments, recessed region 422 may be a region positioned within outer sleeve 402 configured for locking or retaining disposable insertion instrument 100 in a retracted or extended position. For example, in some embodiments, recessed region 422 may have a greater inner diameter than a central portion of axial passage 408. As described in greater detail below, with respect to FIG. 7B, recessed region 422 may comprise a shape, size, or dimensions corresponding to or compatible to receive one or more drive lobes 450 of inner shaft 404. In some embodiments, recessed region 422 may extend a distance d4 and be located a distance d5 from proximal end 412. In some embodiments, the distance d4 is about 10 mm to about 40 mm. Proximal end 412 may have a proximal opening 413 extending a distance d5. In one embodiment, as seen in FIG. 6C, proximal opening 413 may have a cross-sectional shape have scalloped opening with 4 opposed petal cutouts 415 corresponding to the location of four drive lobes 450, and an additional cutout 417 corresponding to the location of distal stop 456 on inner shaft 404. In some embodiments, the shape of proximal opening 413 may be modified depending on the configuration of the drive lobes 450 and distal stop 456.

As seen in FIGS. 7A-7B, drive assembly 400 further comprises an inner shaft 404. In some embodiments, inner shaft 404 may cooperate with outer sleeve 402 to lock disposable insertion instrument 100 in a retracted position, among other functions. In some embodiments, inner shaft 404 may comprise a generally hollow design, or otherwise comprise a channel 460, which is coaxial with axial passage 408. As depicted in FIG. 7A, inner shaft 404 may comprise at least two general portions, inner shaft main body 430 and inner shaft knob 432. In some embodiments, inner shaft main body 430 and inner shaft knob 432 may be molded or manufactured as a singular piece or component. In further embodiments, inner shaft main body 430 and inner shaft knob 432 may be made as individual pieces that may be joined together, such as, for example, screwing inner shaft main body 430 to inner shaft knob 432. Inner shaft main body 430 may comprise a generally tubular design having a proximal end 434 and a distal end 436 defining the channel 460 therebetween. Proximal end 434 may terminate at inner shaft knob 432 and for example, may be molded into inner shaft knob 432. Distal end 436 may be inserted into the axial passage 408 of outer sleeve 402. Accordingly, when assembled, at least a portion of inner shaft main body 430 may be located within axial passage 408 of outer sleeve 402.

In some embodiments, inner shaft knob 432 may provide an engaging surface area to a user or operator, allowing the user or operator to grab and/or manipulate inner shaft 404 and/or drive assembly 400. As depicted, in some embodiments, inner shaft knob 432 may comprise a generally bulbous design, similar to handle 202. Inner shaft knob 432 may further comprise defined sides or angles, providing a gripping surface area to a user or operator. In some embodiments, inner shaft knob 432 may comprise one or more gripping aids 438. For example, the one or more gripping aids 438 may be recessed grooves or embossments. Inner shaft knob 432 may further comprise a diameter or dimensions that are larger than the dimensions of axial passage 408 of outer sleeve 402, thereby preventing inner shaft knob 432 from being received into axial passage 408. Accordingly, in some embodiments, proximal end 434 of inner shaft main body 430 may be adjacent proximal end 412 of outer sleeve 402. Further, in some embodiments, when disposable insertion instrument 100 is in a retracted position, outer sleeve 402 may abut inner shaft knob 432.

In some embodiments, inner shaft knob 432 may comprise proximal opening 470. In some embodiments, proximal opening 470 may be configured as a female receiving end, configured to mate with main body connection end, which may act as a male attachment member. For example, a portion of main body connection end may be inserted into proximal opening 470, thereby providing an overlapping effect between inner shaft handle knob 432 and handle 202. As described in greater detail below, this may aid in aligning one or more openings in inner shaft knob 432 with circumferential groove 208 and the insertion of one or more pins 502. Additionally, in some embodiments, proximal opening 470 may be connected with channel 460, such that elongated main body 218 may enter opening 470 and be inserted into channel 460. Accordingly, as elongated main body 218 is inserted into channel 460, main body connection end may enter opening 470.

As best depicted in FIG. 7A, in some embodiments, inner shaft main body 430 may also comprise one or more drive lobes 450. Drive lobes 450 may be embossments, ridges, or other protrusions extending outward from inner shaft main body 430. The geometric shape and design of drive lobes 450 may vary, but may generally comprise any geometric shape, including for example rounded rectangles. In some embodiments, drive lobes 450 may correspond to the geometric shape and design of recessed region 422. For example, and as described in greater detail below, drive lobes 450 may insert or otherwise fit in recessed region 422.

In some embodiments, inner shaft main body 430 may comprise drive lobes 450 located around the perimeter of inner shaft main body 430. For example, inner shaft main body 430 may comprise four drive lobes 450 spaced apart. In further embodiments, drive lobes 450 may be selectively placed around the perimeter of inner shaft main body 430. For example, inner shaft main body 430 may comprise two sets of two drive lobes 450 (i.e., four total drive lobes) with a first set of two drive lobes 450 placed adjacent to one another and a second set of two drive lobes 450 placed adjacent to one another. The arrangement of the drive lobes 450 may be seen with respect to the proximal end shaft shown in FIG. 6C, wherein each drive lobe 450 would be located circumferentially in line with petal cutouts 415. In some embodiments, some or all drive lobes 450 may have a length of about 25 mm. In some embodiments, some or all drive lobes 450 may have a length of about 20 mm to about 30 mm. It will be appreciated that the examples provided in this paragraph are non-limiting examples, and that the number, placement, and/or spacing of drive lobes 450 may vary. In some embodiments, the one or more drive lobes 450 may be located on inner shaft main body 430 at a distance d6 from proximal end 434. In some embodiments, the distance d6 is about 10 mm to about 25 mm. Inner shaft 404 also includes a distal stop 456, which cooperates with the inner surface of outer sleeve 402 to prevent further advancement of outer sleeve 402. Distal stop 456 may be configured to abut against pin 406 when the outer sleeve 402 is in a distalmost position. In some embodiments, inner shaft also includes a hole 453 used in an injection molding manufacturing process.

FIG. 7B depicts an embodiment of drive assembly 400 in an assembled configuration, with inner shaft 404 and spring 490 received within outer sleeve 402. As described in greater detail below, spring-loaded outer sleeve 402 may be selectively longitudinally movable with respect to inner shaft 404. In some embodiments, to aid in maintaining alignment of outer sleeve 402 during such movement, recessed region 422 may have a greater length than drive lobes 450, such that drive lobes 450 maintain engagement with recessed region 422 in both the retracted and extended positions. The length of recessed region 422 may at least equal the distance that outer sleeve 402 moves during operation. In some embodiments, the recessed region may be about 40 mm. In some embodiments, the recessed region may be about 30 mm to about 50 mm. In some embodiments, the outer sleeve 402 may move longitudinally a distance of about 10 mm to about 20 mm with respect to the inner shaft 404 during operation.

In some embodiments, inner shaft main body 430 may comprise a uniform dimension, such that the outer diameter of inner shaft main body 430 is consistent from proximal end 434 to distal end 436. In further embodiments, as seen in FIG. 7A, inner shaft main body 430 may comprise non-uniform dimensions, such that a first proximal portion of inner shaft main body 430 may have a greater outer diameter than a second distal portion of inner shaft main body 430. For example, in some embodiments, inner shaft main body 430 may comprise an insertion portion 452 and a locking portion 454, wherein insertion portion 452 comprises a smaller outer diameter than locking portion 454. In some embodiments, drive lobes 450 may be located on locking portion 454. In further embodiments, inner shaft main body 430 may comprise a tapered design. For example, in some embodiments, distal end 436 may comprise the smallest outer diameter of inner shaft main body 430 and the outer diameter of inner shaft main body 430 may increase until reaching proximal end 434.

To lock disposable insertion instrument 100 in a retracted position, drive assembly 400 may comprise at least one locking pin 406 within the outer sleeve 402. In order to lock the outer sleeve, 402 in a retracted position, outer sleeve is pulled back against the force of spring 490 and turned in a first direction with respect to inner shaft 404 such that locking pin 406 is captured behind drive lobes 450 on inner shaft 404. In the retracted position, distal end 222 of main body 218 will be exposed such that an implant 1000 may be attached thereto. Once implant 1000 is attached, outer sleeve 402 may be turned in a second direction with respect to inner shaft 404 and locking pin 406 may move distally in a space between the drive lobes 450 such that outer sleeve 402 will move distally as the spring 490 expands.

As described above, in some embodiments, drive assembly 400 may further include a spring 490, providing a spring effect to drive assembly 400 which may aid in selectively transitioning disposable insertion instrument 100 in a retracted position and/or for applying pressure to implant 1000. As depicted in FIGS. 4 and 7B, spring 490 may be located entirely within the interior of drive assembly 400. In some embodiments, spring 490 may be longitudinally located or positioned between a portion of inner shaft 404 and a portion of outer sleeve 402. For example, in some embodiments, spring 490 may have a proximal end 492 that engages with distal end 436 of inner shaft 404 and distal end 494 that engages with a spring retention point 496 of outer sleeve 402. In some embodiments, spring retention point 496 may be a portion of outer sleeve 402 comprising a reduced diameter to prevent spring 490 from traveling further within outer sleeve 402. Spring 490 is positioned concentrically surrounding elongated main body 218 within outer sleeve 402, extending past groove 418 into adapter channel 416.

During the transitioning of disposable insertion instrument 100 to a retracted position, outer sleeve 402 may be moved proximally towards inner shaft knob 432. During this transition, spring 490 may store the built-up elastic potential energy. As described in greater detail below, when outer sleeve 402 is disengaged from inner shaft, the stored elastic potential energy may be applied in a distal direction towards the implant 1000, thereby driving implant 1000 in a distal direction. More specifically, the force of the spring 490 is used to maintain engagement of the adapter 550 with the proximal nut 2000 of the implant 1000 during implantation. Thereby, the proximal nut 2000 may move distally along the implant main body 1012 when the drive assembly 400 is rotated relative to the handle assembly 200, as further described herein.

Figure 9:
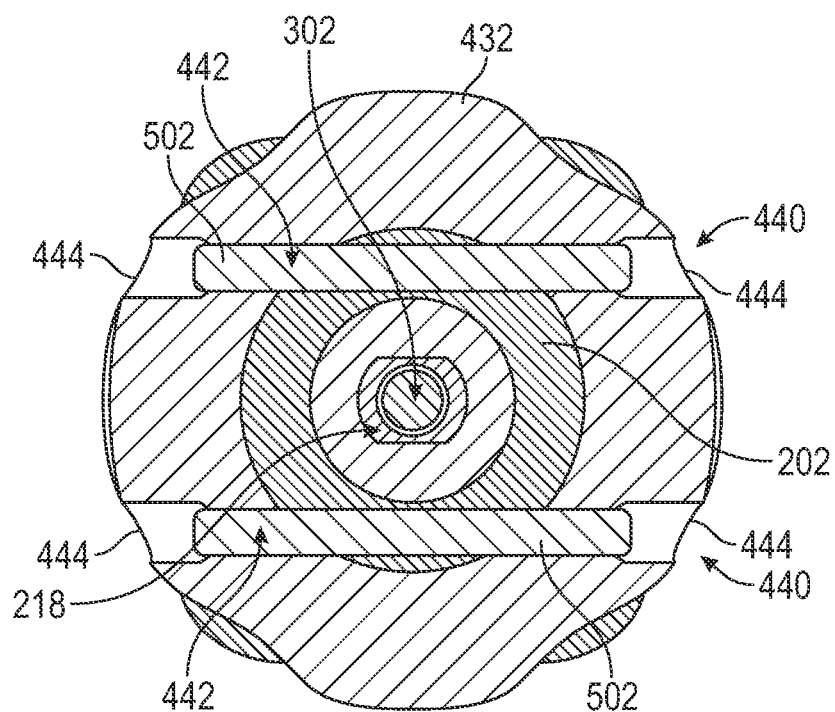
FIG. 9 is a cross-sectional view taken along line 9-9 of FIG. 8 of the coupling handle assembly to drive assembly in accordance with some embodiments of the invention.

In some embodiments, disposable insertion instrument 100 may comprise one or more retaining pins 502 for securing at least a portion of drive assembly 400 to handle assembly 200. As shown in FIGS. 4 and 8-9, in some embodiments, inner shaft knob 432 may comprise one or more pin openings 440. One or more pins 502 may be inserted through pin openings 440 to secure inner shaft knob 432 to handle 202. For example, in some embodiments inner shaft knob 432 may comprise two sets of pin openings 440. In some embodiments, a pin opening 440 may be designed as a channel 442 defined through an entirety of inner shaft knob 432, such that each pin opening 440 comprises two holes 444 with channel 442 connecting the two holes 444. Further, in some embodiments, channel 442 may extend through inner shaft knob 432 and into the space defined by circumferential groove 208. In further embodiments, pin opening 440 may comprise a single hole 444 with channel 442 stopping short of a complete passthrough of inner shaft knob 432. In some embodiments, retaining pins 502 may comprise a length that is shorter in length than the distance between the two holes 444 of a pin opening 440. Accordingly, in some embodiments, when placed, an entirety of retaining pin 502 may be located within the dimensions of inner shaft knob 432. Retaining pins 502 may retain the axial position of inner shaft 404 thereby securing the inner shaft to handle 202. Further, because the two retaining pins 502 may be located at opposing sides of circumferential groove 208, inner shaft 404 and/or handle 202 may rotate around a center point of circumferential groove 208.

As described in greater detail below, in some embodiments, the insertion of implant 1000 may involve the rotation of implant 1000. In some embodiments, rotation of implant 1000 may be achieved through rotation of handle assembly 200 and/or drive assembly 400.

Implant Adapter

Figure 10A:
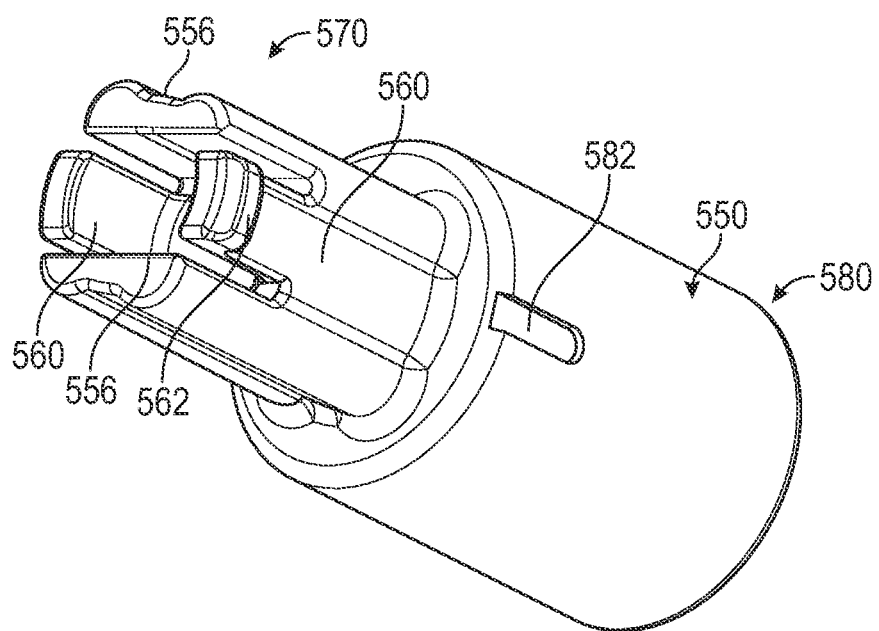
FIG. 10A is a perspective view of an adapter in accordance with an embodiment of the invention.
Figure 10B:
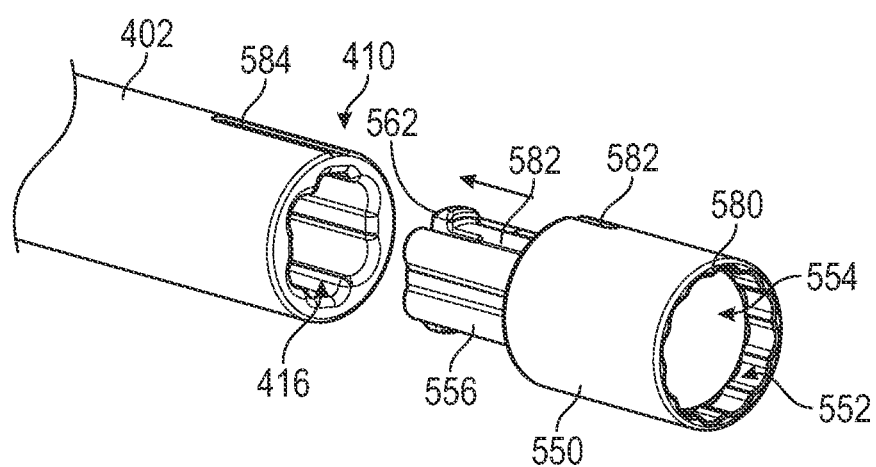
FIG. 10B is an expanded view showing the connection of distal end of the insertion instrument to an implant adapter.
Figure 11A:
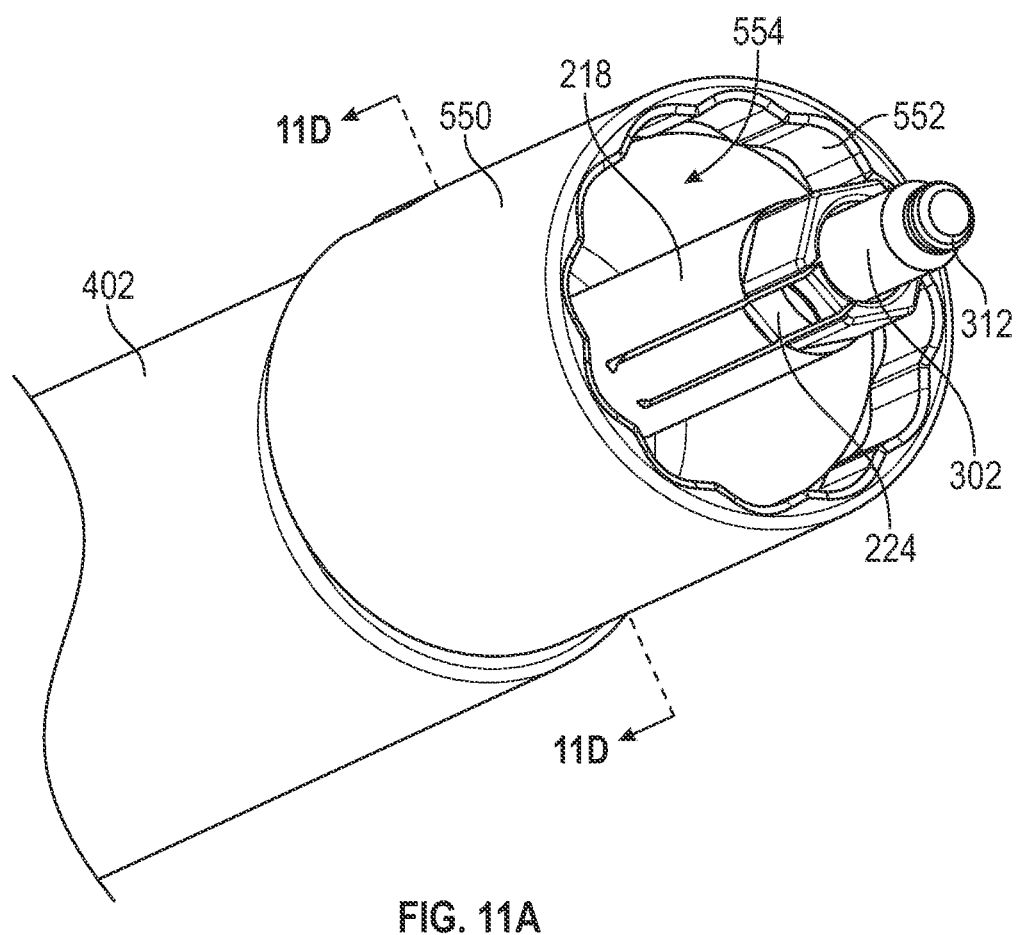
FIG. 11A is an enlarged view of the distal end of insertion instrument showing the elongated main body and the plunger shaft extended from the implant adapter.

With respect to FIGS. 10A-B and 11A-D, in some embodiments, disposable insertion instrument 100 may be paired with an adapter 550, which may be used for attaching implant 1000 to disposable insertion instrument 100. As seen in FIG. 10A-B, adapter 550 includes a proximal end 570 and a distal end 580. Proximal end 570 of adapter 550 is configured to be inserted into adapter channel 416 of outer sleeve 402. Distal end 580 may comprise one or more grooves 552 for coupling to a portion of implant 1000. As seen in FIG. 11A, adapter 550 may further comprise a central axial passage 554, providing a channel for elongated main body 218 and plunger shaft 302 to pass through and extend from.

In some embodiments, as seen in FIG. 10A, adapter 550 may further comprise one or more flexible legs 560 and one or more curved walls 556 located at a proximal end 570 of adapter 550 for engaging with the adapter grooves 420 of adapter channel 416. In further embodiments, one or more flexible legs 560 comprise a locking tab 562 to aid in locking adapter 550 in position. For example, adapter 550 may comprise two locking tabs 562 on two flexible legs 560. The locking tabs 562 may be received within groove 418 on proximal end of adapter channel 416. Accordingly, in some embodiments, adapter 550 may be inserted into adapter channel 416 and secured in place. Adapter 550 includes an alignment line 582 on an outer surface that indicates the location of the legs 560. Outer sleeve 402 also includes an alignment line 584 for aligning with alignment line 582 of adapter 550. Additionally, the one or more flanges 556 may be shaped to cooperate with the one or more adapter grooves 420 present in the adapter channel 416. Accordingly, in some embodiments, adapter 550 may comprise a compatible number of flanges 556 corresponding to the number of recessed regions 422. To remove adapter 550, one may simply pull distally and the locking tabs 562 will release from engagement with grooves 418. The locking tabs 562 cannot be reached from the outside because there are no holes provided in the outer sleeve 402 to access them by a user.

In some embodiments, the one or more grooves 552 may comprise a design that is compatible with any number of particular medical implants 1000. For example, in some embodiments, distal end 580 of adapter 550 may comprise twelve grooves 552, such as a 12 point hex, which may cooperate with a hexagonal nut 2000 on implant 1000 (see FIG. 11B). In one embodiment, distal end 580 may comprise six grooves 552 in a generally hexagonal design. However, distal end 580 of adapter 550 may comprise any number of grooves 552 in any configuration or design. The number and configuration of the one or more grooves 552 may be dependent on factors including, but not limited to, the configuration of implant 1000. As described in greater detail below, the one or more grooves 552 may engage with implant 1000 and may provide a force or pressure to implant 1000. Adapter 550 may be provided in a plurality of sizes for use with implants 1000 of different sizes. In some embodiments, two or three different adapter sizes may be provided, wherein the interior dimensions of the distal end 580 may differ.

Medical Implant

In some embodiments, the disposable insertion instrument 100 may be used to deliver a spinal or other medical implant into the spine, or other part, of a patient. The implant 1000 may take a variety of different configurations and sizes. For example, in some embodiments, the implant 1000 may be useful for treatment of spondylolisthesis, central and foraminal lumbar stenosis, degenerative disc disease and the like. Beneficially, implant 1000 may be percutaneously placed, providing stabilization of the spine, can be used with bone graft material to promote fusion, requires less than a 2.6 cm incision, and can be inserted with local or general anesthesia. As such, the recovery time may be relatively quicker for the patient and the hospital stay may likewise be relatively shorter. An exemplary embodiment of implant 1000 is shown and described with partial features shown and described for the sake of brevity. Further details can be found in application Ser. No. 17/677,677, incorporated by reference herein in its entirety.

Figure 11B:
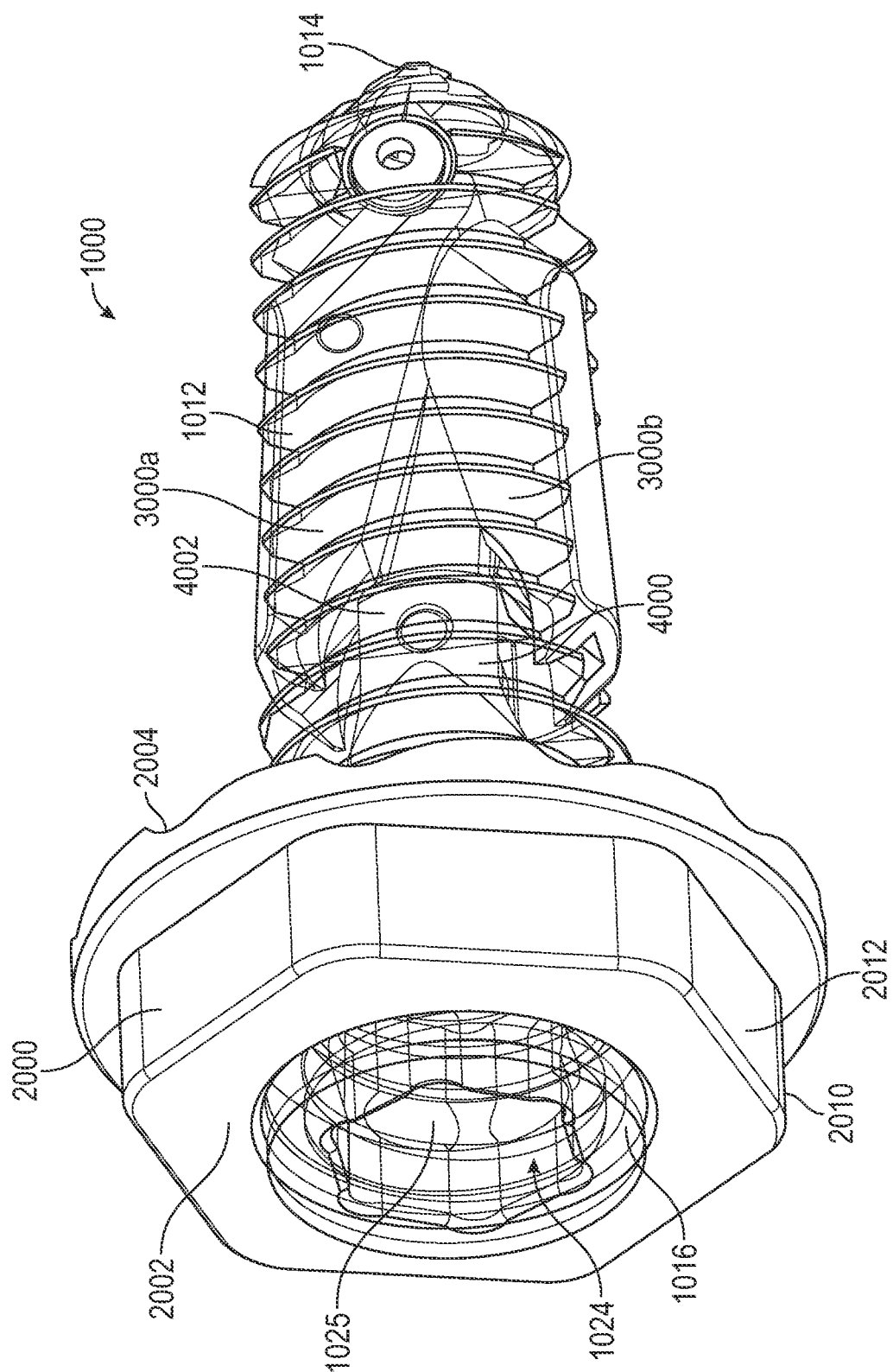
FIG. 11B is a perspective view of an exemplary implant for use with the insertion instrument of the invention.
Figure 11C:
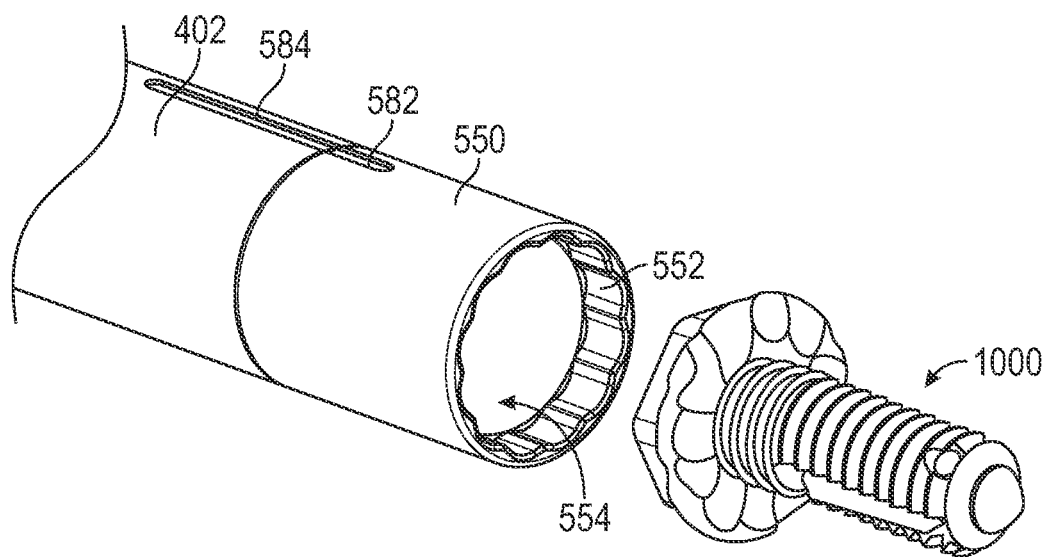
FIG. 11C is an expanded view showing the connection of distal end of the implant adapter to an implant.
Figure 11D:
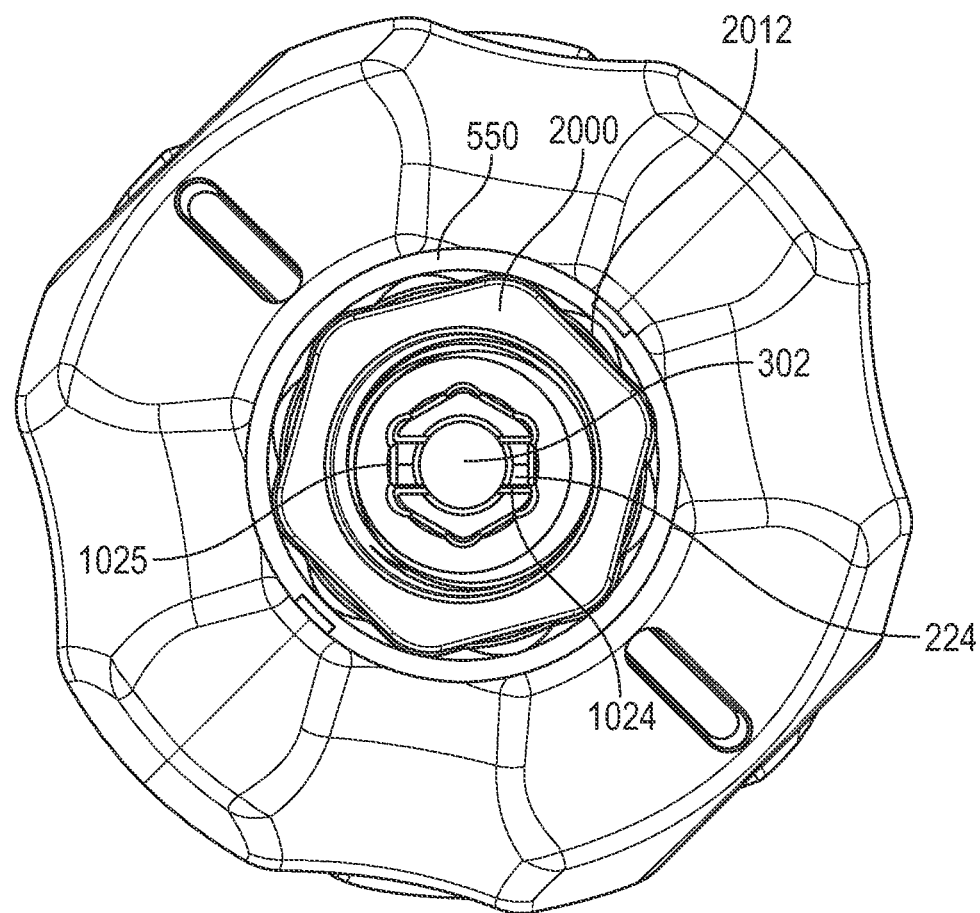
FIG. 11D is a cross-sectional view taken along line 11D-11D of FIG. 11A of the connections of the implant to the insertion instrument.

FIGS. 11B and 12-13 illustrate in detail an exemplary embodiment of an interspinous process implant 1000 for use with the disposable insertion instrument 100. In some embodiments, implant 1000 includes a main body 1012, comprising a distal end 1014 and a proximal end 1016. Implant 1000 further includes a nut 2000 located on the proximal end 1016 of main body 1012 and extendable first and second wings 3000a, 3000b on the distal end 1014 of main body 1012. As can be seen in FIGS. 11B, and 12-13, implant 1000 may further include an implant plunger 4000 and first and second linkages 5000a, 5000b for operatively connecting first and second wings 3000a, 3000b to main body 1012, as will be described herein.

Proximal end 1016 of main body 1012 includes hollow bore 1024. Proximal end of hollow bore 1024 may have a particular shape such as a hexagonal perimeter configured to receive a portion of disposable insertion instrument 100 therein. Specifically, hollow bore 1024 may be configured to receive tip 226 of main body 218. Proximal end of hollow bore 1024 may also include detents 1025 adapted for receiving and engaging with flexible arms 224.

FIG. 12 illustrates implant 1000 with wings 3000a, 3000b in a closed configuration. FIG. 13 illustrates implant 1000 with wings 3000a, 3000b fully deployed with implant 1000 in the open configuration. In some embodiments, implant plunger 4000 may comprise a distal end 4002 and a proximal end. Proximal end may be configured to be located within the bore 1024 of main body 1012 and distal end 4002 is connected to linkages 5000a, 5000b. Implant plunger 4000 may be moved longitudinally within the bore 1024 to open and close wings 3000a, 3000b. Proximal end of implant plunger 4000 may comprise a central bore 4005 for receiving plunger shaft 302 therein. In some embodiments, central bore 4005 of implant plunger 4000 may be threaded on the interior surface to cooperate with the engagement feature 312 on distal end 306 of plunger shaft 302.

As seen in FIG. 11B, in some embodiments, implant 1000 may comprise nut 2000. Nut 2000 can be provided on the proximal end 1016 of main body 1012. Nut 2000 has a proximal side 2002, a distal side 2004, and an internal bore therethrough. In some embodiments, internal bore has interior helical threads for cooperating with helical threads on the exterior surface of main body 1012. In operation, the nut 2000 can be rotated to move the nut 2000 longitudinally along the shaft of main body 1012 such that the distal side 2004 engages tissue and/or bone. In some embodiments, proximal side 2002 has a polygonal extension 2010 with flat sides 2012. Polygonal extension 2010 is shaped to cooperate with implant adapter 550.

In some embodiments, distal side 2004 forms a grip plate having a textured surface. Textured surface may be configured to engage bone or tissue when the implant 1000 is placed in the body to help anchor the implant 1000 in place. When the adapter 550 of insertion instrument 100 is coupled to the nut 2000, rotation of the inner shaft knob 432 moves the nut distally along the threads of main body 1012 to tighten the implant 1000 in place. In some embodiments, nut 2000 can be provided in two sizes—a first size for implants of 8 mm, 10 mm, and 12 mm; and a second size for implants of 14 mm and 16 mm.

Assembly of the Instrument

In some embodiments, one or more of the various sub-assemblies, components, and/or parts of disposable insertion instrument 100 may be assembled prior to the insertion of implant 1000. In further embodiments, a portion of disposable insertion instrument 100 may be assembled, implant 1000 may be attached, and assembly of disposable insertion instrument 100 may be completed. Additionally, in some embodiments, assembly of disposable insertion instrument 100 may include the assembly of one or more of the sub-assemblies. For example, in some embodiments drive assembly 400 may initially start as separate pieces and may need to be assembled. For example, spring 490 may be inserted into axial passage 408 of outer sleeve 402 with distal end 494 engaging with spring retention point 496. After the spring 490 has been inserted and engages with spring retention point 496, inner shaft 404 may be inserted into axial passage 408, starting with distal end 436. Distal end 436 may engage with proximal end 492 of spring 490, and as inner shaft 404 continues insertion through axial passage 408, spring 490 may compress and store elastic potential energy. Inner shaft 404 may continue to be inserted into axial passage 408 until proximal end 412 of outer sleeve generally reaches inner shaft knob 432.

Once proximal end 412 reaches this point, the one or more drive lobes 450 may align with recessed region 422. As outer sleeve 402 slides over inner shaft 404, the one or more drive lobes 450 may be captured by the recessed region 422. For example, as outer sleeve 402 slides over inner shaft 404, the one or more drive lobes 450 may align with recessed region 422. After connecting outer sleeve 402 to inner shaft 404, drive assembly 400 may be ready for assembling with one or more additional sub-assemblies or components.

In some embodiments, adapter 550 may be inserted, attached and secured to distal end 410 of outer sleeve 402. In some embodiments, adapter 550 may be inserted and attached to outer sleeve 402 prior to assembly of drive assembly 400. In further embodiments, adapter 550 may be inserted and attached to outer sleeve 402 after assembly of drive assembly 400. In even further embodiments, adapter 550 may be attached to outer sleeve 402 after drive assembly 400 has been attached to handle assembly 200. To secure adapter 550 to outer sleeve 402, flange 556 of adapter 550 may be inserted into adapter channel 416. During insertion, the one or more flanges 556 of adapter 550 may be received in grooves 420, and the locking tabs 562 may lock into groove 418 to anchor the adapter 550 in place in the adapter channel 416.

In some embodiments, a step of assembling disposable insertion instrument 100 may comprise inserting handle assembly 200 into drive assembly 400. In some embodiments, handle assembly 200 may already be assembled, requiring no further assembly by a user or operator. In further embodiments, handle assembly 200 may be in two or more parts, requiring a user or operator to assemble handle assembly 200 prior to inserting handle assembly 200 into drive assembly 400. For example, in some embodiments, elongated main body 218 may require threading or otherwise connecting to handle 202. In some embodiments, handle assembly 200 may be connected to drive assembly 400 by inserting elongated main body 218 into axial passage 408 of drive assembly 400. Elongated main body 218 may continue to be inserted until handle 202 comes in contact with inner shaft knob 432. In some embodiments, a portion of elongated main body 218 may extend past distal end 410 and/or adapter 550 when outer sleeve 402 of disposable insertion instrument 100 is in a retracted position.

Upon inserting elongated main body 218 into axial passage 408, handle assembly 200 may be secured to drive assembly 400 by retaining pins 502. For example, inner shaft knob 432 may be positioned such that the one or more pin openings 440 are aligned with circumferential groove 208 of handle assembly 200. Once aligned, one or more pins 502 may be inserted into the one or more pin opening 440. The one or more pins 502 may continue to be inserted into the channel 442 of the pin opening 440 until passing through circumferential groove 208 and into an opposing side of inner shaft knob 432. In some embodiments, handle assembly 200 and drive assembly 400 may be secured together through two pins 502. Upon insertion of the one or more pins 502, handle assembly 200 and drive assembly 400 may be secured together.

In some embodiments, plunger assembly 300 may be inserted into handle assembly 200. As described below, in some embodiments, plunger assembly 300 may be inserted into handle assembly after an initial coupling between elongated main body 218 and implant 1000. In some embodiments, plunger assembly 300 may already be assembled, requiring no further action by a user or operator in assembling plunger assembly 300. In further embodiments, one or more parts or components of plunger assembly 300 may start as separate pieces, requiring assembly. For example, in some embodiments, plunger shaft 302 may require coupling to plunger knob 304. Plunger shaft 302 may be threaded into plunger knob 304 or inserted and held in place through an interference fit, by way of non-limiting examples. An assembled plunger assembly 300 may then be inserted into handle assembly 200.

In some embodiments, an assembled plunger assembly 300 may be inserted into handle assembly 200. For example, plunger assembly 300 may be inserted, starting with distal end 306 entering proximal opening 212 of handle 202. Distal end 306 may continue to be inserted through the continuous handle channel until exiting through distal opening 214. In some embodiments, distal end 306 may immediately enter main body lumen 220 of elongated main body 218. Further, distal end 306 may continue to be inserted and extend through main body lumen 220 until exiting the distal end of elongated main body 218. In some embodiments, distal end 306 may further be inserted until exiting from distal end of adapter 550. In some embodiments, when plunger assembly 300 is in its distalmost position, distal end 306 may be the most distally positioned component or part of disposable insertion instrument 100. In some embodiments, plunger knob 304 may be the most proximally positioned component or part of disposable insertion instrument 100.

In some embodiments, implant 1000 may be attached and secured to disposable insertion instrument 100 at various points during assembly of the disposable insertion instrument. For example, in some embodiments, implant 1000 may be positioned on disposable insertion instrument 100 after coupling of drive assembly 400 to handle assembly 200, when drive assembly 400 is in a retracted position, and after adapter 550 has been inserted into adapter channel 416. Accordingly, in some embodiments, implant 1000 may be placed and secured to the exposed distal end 222 of elongated main body 218 when disposable insertion instrument 100 is in a retracted position. Implant 1000 may be directed towards distal end 222, such that distal end 222 enters hollow bore 1024 of implant 1000. When inserted into hollow bore 1024, implant 1000 may continue to be moved towards distal end 222 until detents 1025 of hollow bore 1024 engage with the flexible arms 224 of distal end 222. The engagement of flexible arms 224 and detents 1025 may provide an interference fit between implant 1000 and elongated main body 218, thereby coupling implant 1000 to disposable insertion instrument 100. In some embodiments, the coupling of implant 1000 to elongated main body 218 may also cause a second coupling of nut 2000 of implant 1000 to fit within central axial passage 554 and engage the one or more grooves 552 of adapter 550. As described in greater detail below, the engagement between implant 1000 and adapter 550 may aid in advancing the nut 2000 of implant 1000. In some embodiments, the coupling between elongated main body 218 and implant 1000 may be an initial coupling, with at least one additional coupling available to complete securement of implant 1000 to disposable insertion instrument 100.

In some embodiments, a third coupling between disposable insertion instrument 100 and implant 1000 may be achieved by plunger assembly 300 coupling to implant 1000. For example, as described above, the initial coupling by way of elongated main body 218 and implant 1000 may occur prior to the insertion of plunger assembly 300. Following the initial coupling between elongated main body 218 and implant 1000, plunger assembly 300 may be inserted into or advanced within handle assembly 200 through continuous handle channel 216 and main body lumen 220 until exiting through distal end 222. Upon exiting main body lumen 220, distal end 308 of plunger shaft 302 may engage with implant plunger 4000 of implant 1000. In some embodiments, upon reaching implant plunger 4000, an operator may rotate plunger shaft 302 via plunger knob 304 to thread engagement feature 312 into implant plunger 4000. Plunger shaft 302 may continue to be rotated until engagement feature 312 is completely threaded into implant plunger 4000. As described in greater detail below, once threaded and secured, plunger assembly 300 may be used to manipulate the wings 3000a, 3000b of implant 1000, including for example, transitioning wings 3000a, 3000b between an open and a closed configuration. In some embodiments, plunger assembly 300 may also aid the connection point between handle assembly 200 and implant 1000. For example, when plunger shaft 302 is inserted through main body lumen 220, a portion of plunger shaft 302 may engage with an interior surface of main body lumen 220, including at least distal end 222. This may aid in limiting the inward flexing of flexible arms 224, thereby strengthening the connection between distal end 222 and detents 1025.

In some embodiments, implant 1000 may be secured to disposable insertion instrument 100 at three connection points, i.e., at the connection between handle assembly 200 and implant 1000, the connection between plunger assembly 300 and implant 1000, and the connection between the adapter 550 and implant 1000.

For example, in some embodiments nut 2000 may be positioned within central axial passage 554 such that a portion of nut 2000 is engaged with the one or more grooves 552 of adapter 550. For example, in some embodiments, nut 2000 may comprise a substantially polygonal shape and adapter 550 may comprise complementary grooves 552 configured in a substantially polygonal shape. When positioned in central axial passage 554, the grooves 552 may engage with nut 2000. As described in greater detail below, when outer sleeve 402 is in the extended position, the stored elastic potential energy may cause outer sleeve 402 to apply a constant pressure to nut 2000. This pressure may aid in maintaining contact between adapter 550 and implant 1000 even when implant 1000 is threaded into position. Additionally, the connection between grooves 552 and nut 2000 may aid in rotating nut 2000, which may move nut 2000 distally along the shaft of implant 1000 to engage with the bone in situ.

Process in Use and Implantation

FIGS. 12-13 illustrate insertion and placement of the implant into a target interspinous process space 800. Implant 1000 may be inserted into a patient in a first closed configuration, where implant plunger 4000 is in a proximal position, and wings 3000a, 3000b are in a closed configuration. In one embodiment, for a direct lateral insertion of the implant 1000 into the target interspinous process space 800, an incision may be formed in the skin of a patient. In some embodiments, an introducer tube may be used with disposable insertion instrument 100 to aid in positioning implant 1000. When in position, the implant 1000 is rotated by way of the disposable insertion instrument 100, thus threading the implant 1000 into the target interspinous process space 800, distracting the adjacent spinous processes 802a, 802b, and advancing the implant 1000, generally centered with respect to the spinous processes 802a, 802b.

To rotate the implant 1000, the handle 202 of the handle assembly 200 is rotated in a first direction, such as clockwise, to self-thread the implant 1000 through the interspinous process space 800. Rotation of handle 202 causes the rotation of implant 1000 through the connection between tip 226 and hollow bore 1024, wherein the rotation force is transferred from elongated main body 218 to implant 1000. During the rotation of the implant 1000, the implant 1000 distracts the interspinous space 800. For example, during rotation, threads of main body 1012 may distract the interspinous space 800, tightening and locking implant 1000 in position in the interspinous space 800. Relative rotation and axial translation between the implant 1000 and the disposable insertion instrument 100 is inhibited because the implant 1000 is locked onto the tip 226 by the flexible arms 224 of the handle assembly 200. Distraction can also be performed in advance by a separate instrument, with insertion of the implant 1000 following, and maintaining such distraction.

When implant 1000 has been inserted into interspinous space 800 far enough so that anchoring wings 3000a, 3000b have passed through the interspinous space 800, the anchoring wings 3000a, 3000b can be deployed. Due to the coupling of plunger shaft 302 and implant plunger 4000, the plunger shaft 302 may be moved longitudinally to deploy or open wings 3000a, 3000b. With implant 1000 in position, a force or pressure may be applied to plunger knob 304 to move plunger shaft 302 distally. This distal movement will also cause implant plunger 4000 to move distally, such that linkages 5000a, 5000b separate, and the wings 3000a, 3000b rotate into an open configuration.

In some embodiments, deployment of wings 3000a, 3000b may not result in the complete engagement of implant 1000 with the bone and/or tissue of the implant site. For example, after deployment of wings 3000a, 3000b, there may be a space or a gap between wings 3000a, 3000b and the bone and/or tissue at the implant site. Accordingly, in some embodiments, nut 2000 may be moved distally, such as by rotation, to engage the bone and/or tissue as well as forming a proximal anchor. Specifically, after the distal movement, nut 2000 may engage a first lateral surface of a first spinous processes 802a and a second lateral surface of a second spinous process 802b. Additionally, wings 3000a, 3000b may engage a third opposite surface of first spinous process 802a and a fourth opposite surface of second spinous process 802b. Additionally, wings 3000a, 3000b may include fangs or spikes to engage with the bone and/or tissue at the implant site forming a distal anchor. In some embodiments, the wings 3000a, 3000b and the nut 2000 can be engaged on opposite side of the spinal process when the implant 1000 is in place.

In some embodiments, rotation of nut 2000 may be achieved through rotation of drive assembly 400 and the contact between adapter 550 and implant 1000. For example, during the insertion process, outer sleeve 402 may be in the extended position. Upon disengagement of the locking pin 406 from behind the drive lobes 450, the stored elastic potential energy in spring 490 causes distal movement of outer sleeve 402. This distal movement may act upon implant 1000, thereby maintaining a consistent contact between adapter 550 and implant 1000. To rotate nut 2000, an operator may apply a rotational force to inner shaft knob 432 and rotate the entire drive assembly 400. This rotational movement causes the distally connected adapter 550 to rotate as well. Because of the engagement between nut 2000 and the one or more grooves 552 of adapter 550, nut 2000 may rotate in response.

After deployment of implant 1000 in interspinous region, the disposable insertion instrument 100 may be detached from implant 1000 and removed, thereby leaving implant 1000 intact and in position in the patient. For example, a first step of disengaging disposable insertion instrument 100 may involve the rotation of plunger assembly 300 to unscrew engagement feature 312 from implant plunger 4000. For example, using plunger knob 304, plunger shaft 302 may be rotated in a second opposite direction, such as counterclockwise, to unscrew plunger shaft 302. Upon unscrewing and disengagement, plunger assembly 300 may be partially retracted or fully removed from disposable insertion instrument 100.

As described above, in some embodiments, when inserted, plunger shaft 302 may aid in preventing the inward flexing of flexible arms 224. After plunger assembly 300 has been retracted or removed from distal end of disposable insertion instrument 100, handle assembly 200 may be disengaged and/or removed from implant 1000. For example, a longitudinal proximal force or action may be applied to handle 202, thereby decoupling flexible arms 224 from the detents 1025 of hollow bore 1024. At the same time, adapter 550 may be disengaged from nut 2000 by proximal longitudinal motion. Once disengaged, disposable insertion instrument 100 may no longer be coupled to implant 1000 and may be removed from the patient. Once removed, the disposable insertion instrument 100 may be disposed of in a safe and sterile manner.

In some embodiments, disposable insertion instrument 100 may be a single-use, disposable tool, such that after a single use, the disposable insertion instrument 100 may be disposed of. In some embodiments, insertion instrument 100 may also be sterilized after use. Accordingly, in some embodiments, the various sub-assemblies of disposable insertion instrument 100 may be constructed from materials that are designed to be used primarily for a single use. For example, in some embodiments, the various sub-assemblies of disposable insertion instrument 100 may be constructed, fabricated, or manufactured from synthetic polymers (e.g., polyacrylamide or IXEF®), three-dimensional printed materials (e.g., RULON, PEEK), plastics, among other materials. In some embodiments, a first sub-assembly or set of parts may be made from a first material and a second sub-assembly or set of parts may be made from a second material that is different from the first material. However, it will be appreciated that in further embodiments, disposable insertion instrument 100 may be made from other materials that are not primarily used for single-use, and may be constructed, fabricated, 3D printed, or manufactured from medical grade stainless steel, alloys, and/or polymers (e.g., RULON, PEEK) or another like durable material. For example, in some embodiments, disposable insertion instrument 100 may not be a disposable tool, and instead, may be configured to be used multiple times. In some embodiments, the various sub-assemblies, parts, and/or components of disposable insertion instrument 100 may be manufactured using a variety of different methods, including but not limited to molding, additive manufacturing, machining, among other methods. Further, in some embodiments, certain parts or components may require materials that are able to withstand certain thresholds of force, torque, or pressure, and may be constructed from metal, steel, aluminum, or other durable materials. Even further, in some embodiments, certain sub-assemblies, parts, and/or components may be manufactured using one method of construction and other sub-assemblies, parts, and/or components may be manufactured using a different method of construction.

Many different arrangements of the various components depicted, as well as components not shown, are possible without departing from the scope of the claims below. Embodiments have been described with the intent to be illustrative rather than restrictive. Alternative embodiments will become apparent to readers of this disclosure after and because of reading it. Alternative means of implementing the aforementioned can be completed without departing from the scope of the claims below. Certain features and sub combinations are of utility and may be employed without reference to other features and sub-combinations and are contemplated within the scope of the claims. Although various embodiments have been described with reference to the embodiments illustrated in the attached drawing figures, it is noted that equivalents may be employed, and substitutions made herein without departing from the scope of the recited claims.

Although the invention has been described with reference to the embodiments illustrated in the attached drawing figures, it is noted that equivalents may be employed, and substitutions made herein without departing from the scope of the invention as recited in the claims. Having thus described various embodiments of the invention, what is claimed as new and desired to be protected by Letters Patent includes the following:

What is claimed is:

1. An insertion instrument for inserting an implant, the insertion instrument comprising:
    a handle assembly comprising:
        a handle knob comprising a distally located circumferentially extending groove;
        an elongated main body extending distally away from the handle knob; and
        a lumen extending from a proximal end of the handle knob to a distal end of the elongated main body,
        wherein the distal end of the elongated main body is adapted for engaging with an implant;
    a plunger assembly slidably received within the lumen of the handle assembly, the plunger assembly comprising a plunger knob and a plunger shaft, wherein a distal end of the plunger shaft is configured to engage the implant; and
    a spring-loaded drive assembly comprising:
        an outer sleeve comprising at least one recessed region;
        an inner shaft comprising:
            an inner shaft knob comprising at least one retaining pin opening aligned with the distally located circumferentially extending groove;
            an inner shaft main body;
            at least one drive lobe comprising a raised region on an exterior circumference of the inner shaft main body;
        at least one retaining pin,
        wherein the at least one retaining pin is insertable into the at least one retaining pin opening and is further received by the distally located circumferentially extending groove, operatively coupling the inner shaft to the handle knob; and
        a locking pin,
        wherein the spring-loaded drive assembly comprises a first extended position and second retracted position, wherein the locking pin is located proximally of the at least one drive lobe in the second retracted position, and wherein the locking pin is located adjacent to the at least one drive lobe in the first extended position, and
        wherein the at least one drive lobe is received within the at least one recessed region in the second retracted position.

2. The insertion instrument of claim 1, wherein the at least one drive lobe comprises at least two drive lobes, the locking pin is fixedly mounted to the outer sleeve, and the locking pin is located between the at least two drive lobes in the first extended position.

3. The insertion instrument of claim 1, wherein the outer sleeve is configured to be rotated and moved proximally with respect to the inner shaft to move the spring-loaded drive assembly from the first extended position to the second retracted position.

4. The insertion instrument of claim 1, wherein the distal end of the plunger shaft comprises external threading configured to engage an implant plunger of the implant, and wherein the distal end of the elongated main body comprises a hexagonal extension configured to engage a proximal bore of the implant.

5. The insertion instrument of claim 1, wherein the inner shaft main body comprises an inner lumen therethrough, and the elongated main body is received within the inner lumen of the inner shaft main body.

6. The insertion instrument of claim 1, wherein the inner shaft comprises two retaining pin openings, the spring-loaded drive assembly comprises two retaining pins, and the two retaining pins are retained on opposing sides of the distally located circumferentially extending groove via the two retaining pin openings.

7. The insertion instrument of claim 6, wherein the inner shaft of the spring-loaded drive assembly is configured to rotate around a center point of the distally located circumferentially extending groove.

8. The insertion instrument of claim 1, wherein the at least one drive lobe comprises a first set of drive lobes and a second set of drive lobes spaced equidistantly apart on an exterior surface of the inner shaft main body, wherein each of the first set of drive lobes and the second set of drive lobes comprises two drive lobes.

9. The insertion instrument of claim 8, wherein the outer sleeve comprises a first recessed region and a second recessed region, wherein the first recessed region receives the first set of drive lobes, and the second recessed region receives the second set of drive lobes.

10. The insertion instrument of claim 1, wherein the spring-loaded drive assembly further comprises a spring located at the distal end of the inner shaft main body, wherein the spring-loaded drive assembly is in the first extended position when the spring is relaxed, and the spring-loaded drive assembly is in the second retracted position when the spring is compressed.

11. The insertion instrument of claim 10, wherein the outer sleeve further comprises a retention point, and wherein a first end of the spring engages with the distal end of the inner shaft main body and a second end of the spring engages with the retention point.

12. A medical implant insertion system comprising:
a handle assembly comprising:
a handle knob comprising at least one retaining pin opening;
an elongated main body extending distally away from the handle knob;
a main body lumen extending from a proximal end of the handle knob to a distal end of the elongated main body,
wherein the distal end of the elongated main body is adapted for engaging with an implant;
a plunger assembly slidably received within the main body lumen of the handle assembly, the plunger assembly comprising a plunger knob and a plunger shaft, wherein a distal end of the plunger shaft is configured to engage the implant; and
a spring-loaded drive assembly comprising:
an outer sleeve comprising at least one recessed region;
an inner shaft comprising:
an inner shaft knob comprising a proximally located circumferentially extending groove aligned with the at least one retaining pin opening;
an inner shaft main body;
at least one drive lobe on the inner shaft main body, said at least one drive lobe being received within the at least one recessed region;
at least one retaining pin,
wherein the at least one retaining pin is insertable into the at least one retaining pin opening and is further received by the proximally located circumferentially extending groove, operatively coupling the inner shaft to the handle knob; and
a locking pin,
wherein the spring-loaded drive assembly comprises a first extended position and second retracted position, wherein the locking pin is located proximally of the at least one drive lobe in the second retracted position, and wherein the locking pin is located adjacent to the at least one drive lobe in the first extended position, and
wherein at least one drive lobe is received within the at least one recessed region in the second retracted position; and
an implant adapter comprising a proximal end and a distal end,
wherein the proximal end of the implant adapter comprises at least one flexible leg reversibly attached to a distal end of the outer sleeve of the spring-loaded drive assembly, and wherein the distal end of the implant adapter is configured to engage the implant.

13. The medical implant insertion system of claim 12, wherein the implant adapter comprise four flexible legs and the distal end of the outer sleeve comprises four adapter grooves for receiving the four flexible legs.

14. The medical implant insertion system of claim 13, wherein the implant adapter further comprises a plurality of grooves in a hex configuration for engaging with a hexagonal nut of the implant.

15. A method of inserting a medical implant using an insertion instrument, the method comprising:
providing the insertion instrument comprising:
a handle assembly comprising:
a handle knob comprising a distally located circumferentially extending groove;
an elongated main body extending distally away from the handle knob;
a main body lumen extending from a proximal end of the handle knob to a distal end of the elongated main body,
wherein the distal end of the elongated main body is adapted for engaging with an implant;
a plunger assembly slidably received within the main body lumen of the handle assembly, the plunger assembly comprising a plunger knob and a plunger shaft, wherein a distal end of the plunger shaft is configured to engage the implant; and
a spring-loaded drive assembly comprising:
an outer sleeve comprising a drive lumen with a recessed region;
an inner shaft comprising:
an inner shaft knob comprising at least one retaining pin opening aligned with the distally located circumferentially extending groove;
an inner shaft main body;
at least one drive lobe comprising a raised region on an exterior circumference of the inner shaft main body; and
an inner lumen;
at least one retaining pin,
wherein the at least one retaining pin is insertable into the at least one retaining pin opening and is further received by the distally located circumferentially extending groove; and
a locking pin;
receiving the inner shaft main body within the drive lumen of the outer sleeve of the spring-loaded drive assembly, wherein the at least one drive lobe is received within the recessed region;

receiving the elongated main body of the handle assembly within the inner lumen of the inner shaft main body of the spring-loaded drive assembly; and receiving the plunger shaft within the main body lumen of the elongated main body such that the plunger shaft is longitudinally movable therein.

16. The method of claim 15, further comprising:

attaching an implant adapter to a distal end of the outer sleeve of the spring-loaded drive assembly;

retracting the outer sleeve of the spring-loaded drive assembly against a force of a spring such that the distal end of the elongated main body extends distally from the distal end of the implant adapter; and rotating the outer sleeve with respect to the inner shaft of the spring-loaded drive assembly, such that a locking pin is seated proximally of the at least one drive lobe to maintain the outer sleeve in a retracted position.

17. The method of claim 16, further comprising:

while the outer sleeve is locked in the retracted position, attaching the implant to the elongated main body;

the implant comprising: an implant main body, at least one expandable distal wing connected by linkages to an implant plunger, and a proximal nut; and inserting the distal end of the elongated main body into a proximal bore of the implant while the plunger shaft is in the retracted position.

18. The method of claim 17, wherein the distal end of the elongated main body includes flexible arms, and wherein attaching the implant further comprises:

advancing the plunger shaft distally to engage the implant and lock the flexible arms of the elongated main body to the implant.

19. The method of claim 18, wherein attaching the implant further comprises:

inserting the distal end of the plunger shaft into an implant plunger bore of the implant plunger;

rotating the plunger shaft to engage internal threads of the implant plunger bore with external threads of the plunger shaft; and connecting the distal end of the implant adapter to the implant by receiving the proximal nut of the implant in a plurality of adapter grooves of the implant adapter.

20. The method of claim 19, further comprising:

inserting the distal end of the insertion instrument to a target region of a patient, upon reaching the target region, rotating the handle assembly to thread the implant into bone;

longitudinally advancing the plunger shaft to deploy the at least one expandable distal wing of the implant; and rotating the spring-loaded drive assembly with respect to the handle assembly to rotate the proximal nut on the implant.

\* \* \* \* \*